US012077495B2

(12) United States Patent
Klein et al.

(10) Patent No.: US 12,077,495 B2
(45) Date of Patent: Sep. 3, 2024

(54) COMPOUNDS FOR THE TREATMENT OF ACUTE BRAIN INJURY

(71) Applicants: Københavns Universitet, Copenhagen K (DK); Otago Innovation Ltd, Dunedin (NZ)

(72) Inventors: Anders Bue Klein, Søborg (DK); Andrew Neil Clarkson, Dunedin (NZ); Joshua Macdonald Houlton, Dunedin (NZ); Ulrike Leurs, Copenhagen (DK); Rasmus Prætorius Clausen, København S (DK); Bente Frølund, Charlottenlund (DK); Petrine Wellendorph, Kgs. Lyngby (DK)

(73) Assignees: Københavns Universitet, Copenhagen K (DK); Otago Innovation Ltd., Dunedin (NZ)

( * ) Notice: Subject to any disclaimer, the term of this patent is extended or adjusted under 35 U.S.C. 154(b) by 1072 days.

(21) Appl. No.: 16/965,343

(22) PCT Filed: Feb. 1, 2019

(86) PCT No.: PCT/DK2019/050041
§ 371 (c)(1),
(2) Date: Jul. 28, 2020

(87) PCT Pub. No.: WO2019/149329
PCT Pub. Date: Aug. 8, 2019

(65) Prior Publication Data

US 2021/0122700 A1 Apr. 29, 2021

(30) Foreign Application Priority Data

Feb. 2, 2018 (DK) .......................... PA 2018 70067

(51) Int. Cl.
*C07C 69/757* (2006.01)
*A61P 25/00* (2006.01)
(Continued)

(52) U.S. Cl.
CPC ............ *C07C 69/757* (2013.01); *A61P 25/00* (2018.01); *C07C 59/54* (2013.01); *C07C 59/56* (2013.01); *C07C 69/732* (2013.01)

(58) Field of Classification Search
CPC ..... C07C 69/757; C07C 69/732; C07C 59/54; C07C 59/56
See application file for complete search history.

(56) References Cited

U.S. PATENT DOCUMENTS 5,466,715 A 11/1995 Washburn et al.

FOREIGN PATENT DOCUMENTS

CN 103533949 A 1/2014
IT 1312362 B1 4/2002
(Continued)

OTHER PUBLICATIONS

Ungnade et al., 16 J. Org. Chem. 1311-17 (1951) (Year: 1951).*
(Continued)

*Primary Examiner* — Timothy R Rozof
(74) *Attorney, Agent, or Firm* — Julie K. Staple; Dinsmore & Shohl LLP

(57) ABSTRACT

The invention relates to a compound according to formula I wherein when $R_5$ is H, and $R_1$ and $R_2$ form a ring system, then said compound is selected from the following compounds of formula II or formula IV or when $R_2$ is H, and $R_1$ and $R_5$ form a ring system, then said compound has formula III.

(Continued)

(I)

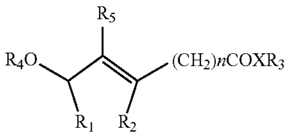

(II)

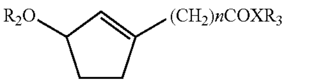

(IV)

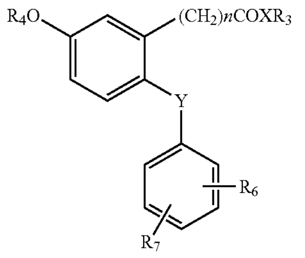

(III)

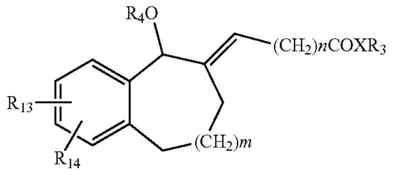

19 Claims, 18 Drawing Sheets

Figure 1:
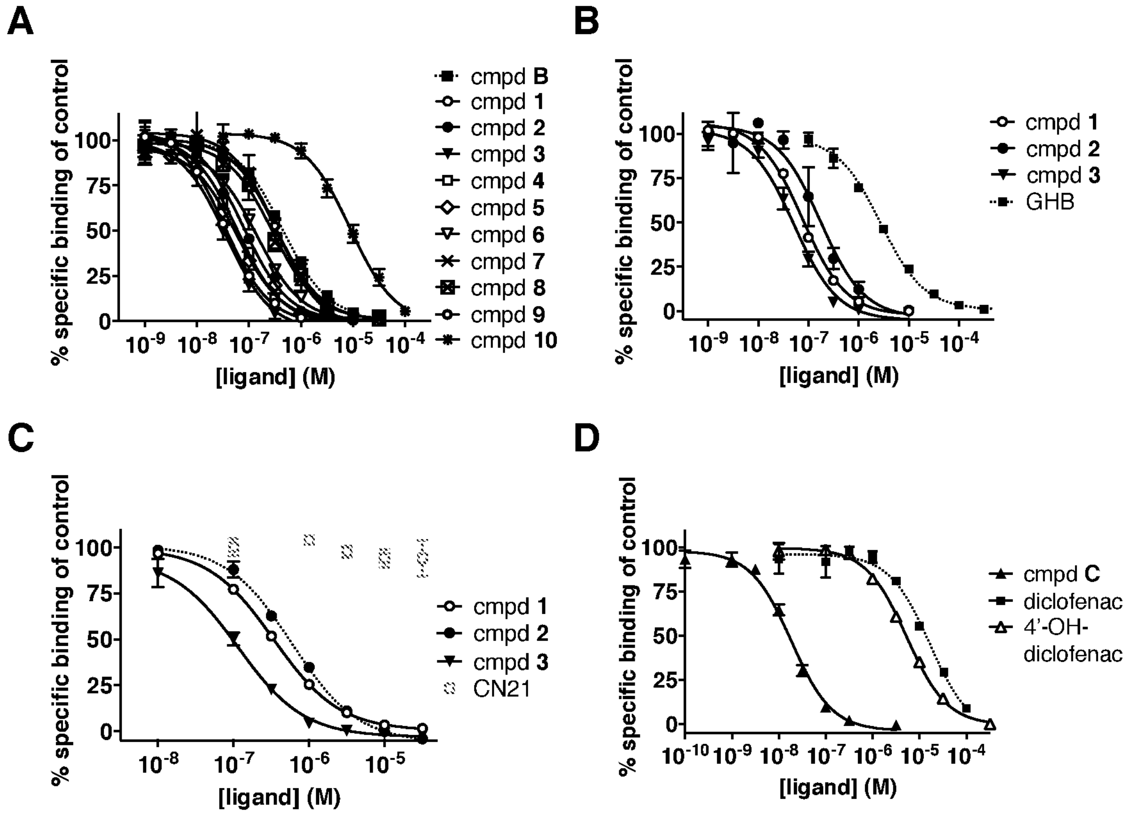

Specification includes a Sequence Listing.

(51) Int. Cl.

| | |
|---|---|
| ***C07C 59/54*** | (2006.01) |
| ***C07C 59/56*** | (2006.01) |
| ***C07C 69/732*** | (2006.01) |

(56) References Cited

FOREIGN PATENT DOCUMENTS

| | | |
|---|---|---|
| JP | 2010-500351 | 1/2010 |
| WO | 2008/021029 A2 | 2/2008 |
| WO | 2013/024028 A1 | 2/2013 |

OTHER PUBLICATIONS

Bowman et al., (1) J. Chem. Soc., Perkins Trans. 1 Org. & Bio. Org. Chem. 1-4 (1972-1999) (1973) (Year: 1973).*

Pang et al., 29(7) Chem. Res. Toxicology, 1118-1131 (2016) (Year: 2016).*

Atkinson et al. Substituted (2-Phenoxyphenyl) acetic Acids with Antiinflammatory Activity. J. Med. Chem, 26: 1353-1360, 1983.

Database Registry (Online), 2011.01.27RN: 1260881-11-5.

Buka et al., a- and y-substitution reactions fo cyclic y-acetoxy-a, B-unsaturated esters with a novel reagent RuCu—Alcl3. Synthetic Communications, 10(2): 119-125, 1980.

Kraii et al., Molecular Hybridization of potent and selective y-Hydroxybutyric Acid (GHB) Ligands: Design, synthesis, binding studies, and Molecular Modeling of Novel 3-Hydroxycyclopent-1-enecarboxylic Acid (HOCPCA) and trans-y-Hydroxycrotonic Acid (T-HCA) Analogs. J. Med. Chem., 60: 9032-9039, 2017.

Marek et al., The labeling of unsaturated y-hydroxybutyric acid by heavy isotopes of hydrogen: iridium complex-mediated H/D exchange by C—H bond activation vs reduction by boro-deuterides/tritides. J. Label Compd. Radiopharm, 59: 476-483, 2016.

Stork et al., An efficient synthesis of (+/−) methyl epijasmonate via the radical-mediated haloacetal cyclization. New J. Chem, 16: 95-98, 1992.

Venkataraman et al., Application of engineered cytochrome P450 mutants as biocatalysts for the synthesis of benzylic and aromatic metabolites of fenamic acid NSAIDs. Bioorg. Med. Chem., 22: 5613-5620, 2014.

Anonymous, "Compound summary AYJDLOZBQLZXMSUHFF-FAOYSA-N", PubChem, retrieved from https://pubchem.ncbi.nlm.nih.gov/compound/91875603#section=top.

Aye et al., Parallel kinetic resolution of tert-butyl (RS)-3-oxy-substituted cyclopent-1-ene-carboxylates for the asymmetric synthesis of 3-oxy-substituted cispentacin and transpentacin derivatives, Organic And Biomolecular Chemistry, 6(12): 2195-2203, 2008.

Bay et al., GHB receptor targets in the CNS: Focus on high-affinity binding sites, Biochemical Pharmacology, 8(2): 220-228, 2013.

Brenna et al., Biocatalytic synthesis of chiral cyclic [gamma]-oxoesters by sequential C—H hydroxylation, alcohol oxidation and alkene reduction, Green Chemistry, 19(21): 5122-5130, 2017.

Database Registry [Online] Chemical Abstracts Service, Columbus, Ohio, US, Jun. 15, 2015, retrieved from STN accession No. 1780717-73-8, database accession No. 1780717-73-8.

Database Registry [Online] Chemical Abstracts Service, Columbus, Ohio, US, Nov. 16, 1984, retrieved from STN accession No. 73934-74-4, database accession No. 73934-74-4.

Database Registry [Online] Chemical Abstracts Service, Columbus, Ohio, US, Oct. 9, 1992, retrieved from STN accession No. 143893-17-8, database accession No. 143893-17-8.

Fonteneau et al., Chemoenzymatic synthesis of enantiopure isopropyl (3R)- and (3S)-3-hydroxycyclohex-1-ene-1-carboxylates and their reduction to isomers of isopropyl 3-hydroxy-cyclohexane-1-carboxylate, Tetrahedron Asymmetry, 13(6): 579-585, 2002.

Jin et al., Effect of gamma-hydroxybutyric acid receptor on focal cerebral ischemia-reperfusion injury in rats, Acta Pharmaceutica Sinica, 42(8): 838-842, 2007.

Lee et al., Free radical-mediated ring expansion reactions: endocyclic cleavage of cyclopropylcarbinyl radicals, Bull. Korean Chem. Soc., 21(6): 595-603, 2000.

Sun et al., A new route into hexahydro-cyclopenta[b]pyrrole-cis-3a.6-diols. Synthesis of constrained bicyclic analogues of pyrrolidine azasugars, Tetrahedron, 61(44): 10462-10469, 2005.

Vogensen et al., New Synthesis and Tritium Labeling of a Selective Ligand for Studying High-Affinity [gamma]-Hydroxybutyrate (GHB) Binding Sites, Journal Of Medicinal Chemistry, 56(20): 8201-8205, 2013.

English translaton of IT1312362.

English translation of Jin et al., Effect of gamma-hydroxybutyric acid receptor on focal cerebral ischemia-reperfusion injury in rats, Acta Pharmaceutica Sinica, 42(8): 838-842, 2007.

Sadasivan, S. et al., y-Hydroxybutyrate (GHB), y-Butyrolactone (GBL), and 1,4-Butanediol (1,4-BD) Reduce the Volume of Cerebral Infarction in Rodent Transient Middle Cerebral Artery Occlusion, Ann. N.Y. Acad. Sci., 1074: 537-544, 2006.

First Office Action for Chinese Application No. 2019800114516, dated Feb. 23, 2023.

Pan et al., Protection of GHBA on the Ischemic Insult of Focal Cerebral Ischemia Reperfusion, Chin J Clin Neurosci, 8(3): 172-174, 2000.

Notice of Reasons for Refusal for Japanese Patent Application No. 2020-542088 dated Feb. 14, 2023.

* cited by examiner

A

B

COMPOUNDS FOR THE TREATMENT OF ACUTE BRAIN INJURY

FIELD OF THE INVENTION

The present invention relates to novel compounds that are suitable for use in the treatment of acute brain injury. The invention also relates to use of already known compounds such as compound A, B, C and D for use in the treatment of acute brain injury.

INTRODUCTION TO THE INVENTION

Injuries to the brain or spinal cord (termed Central Nervous System, CNS) from episodes of reduced blood flow such as stroke, trauma or neurodegenerative disorders produce loss of behavioural function and limited recovery. The loss of function generally occurs in two ways. First, the injury causes complete damage at the center of the insult, resulting in damage to neural circuits that control a bodily function, such as movement, sensation, memory or language. Second, the injury causes partial damage to neural circuits that are adjacent to the injury site (termed peri-infarct cortex), and disables the function of these circuits.

Stroke, which can be either ischemic or haemorrhagic in nature, is a major worldwide health issue, often resulting in long-term disability. As the population ages, the number of stroke patients will increase, contributing to a significant social and economic burden on society. To date, the only medical therapy available is administration of tissue plasminogen activator (tPA), i.e. thrombolysis, which must be given within a 4.5-hr time window after the onset of stroke. Thus, there is a large, unmet need for neuroprotective compounds that can halt neuronal death in the early phase of brain ischemia.

CURRENT STATE OF THE ART

The current state of the art in pharmacological stroke treatment is limited to acute intravenous administration of the thrombolytic drug tPA. tPA works by dissolving blood clots and opening brain blood vessels. tPA is thus a "neuroprotective" therapy because it works by restoring blood flow and preventing the expansion of ischemic cell death in the brain following acute injury. tPA confers a modest behavioral benefit in functional recovery, but has a very narrow therapeutic window. tPA must be delivered within 4.5 hrs from the time the patient suffers a stroke, otherwise the risks associated with tPA administration outweigh any potential benefit. At present this time window precludes administration of tPA to approximately 90% of all stroke patients. Furthermore, this treatment is effective only in a subset of stroke patients. For example, tPA is not an appropriate treatment option following haemorrhagic stroke, as the "clot bursting" features of the drug can exacerbate the bleeding in this type of stroke. Therefore, having a compound that extends the narrow therapeutic window for treatment and facilitates an improvement in neurological function is of great need.

DESCRIPTION OF THE INVENTION

The high unmet need for agents to protect the CNS from neurodegeneration or injury caused by trauma and conditions of local cerebral or global hypoperfusion (e.g. stroke, haemodynamic shock with cardiac arrest, heart failure or during surgery) has prompted researchers to search for new druggable targets. Compounds targeting N-methyl-D-aspartate (NMDA) receptors and/or having anti-inflammatory properties have shown promising results in pre-clinical models and have led to extensive clinical testing. Regrettably, nearly all of these compounds have failed in clinical trials and blood-clot resolving agents remain the only approved pharmacological treatment. The shortcoming of the various tPA treatments include the rather limited window of treatment, which is within 4.5 hrs after stroke and the possibility of haemorrhagic malformation. Due to the typical delay between the occurrence of an ischemic stroke and medical attention, this type of treatment is often contraindicated. Thus, other compounds are needed in order to halt and prevent neuronal death after an ischemic stroke within a clinically relevant time frame.

GHB (γ-hydroxybutyric acid) is a naturally occurring GABA (γ-aminobutyric acid) metabolite and a neuromodulator that is present in micromolar concentrations in the mammalian brain. GHB (sodium oxybate) is used both clinically as a prescribed drug in narcolepsy, and as a recreational drug (e.g. Fantasy). GHB displays both low affinity (millimolar) binding to $GABA_B$ receptors and high affinity (nanomolar to micromolar) binding to a specific protein in neurons. Mediated by $GABA_B$ receptors, one well-established pharmacological effect of GHB is a lowering of body temperature (Kaupmann et al., 2003). By contrast, the neuro-physiological and -pharmacological effects related to the high-affinity binding site are still unknown, because the precise molecular identity of this binding site has been elusive.

The present invention provides compounds having the following general formula (formula I):

(formula I)

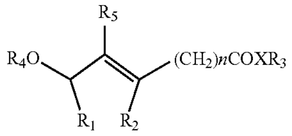

wherein, when $R_5$ is H, and $R_1$ and $R_2$ form a ring system, then said compound is selected from the following compounds of formula II or formula IV (formula II)

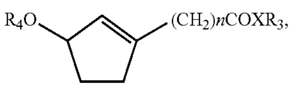

or (formula IV)

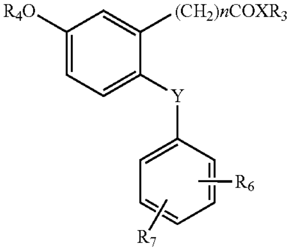

wherein n is 0 or 1;

X is selected from O or NH

Y is NH, O, S, $CH_2$ $R_3$ is selected from H, linear or branched $C_1$-$C_6$-alkyl including -Me, -Et, —Pr, -iPr, -Bu, -iBu, -tBu, pentyl, neopentyl, hexyl, branched hexyl; -benzyl, polyethylenglycolyl (PEG), or a group such as

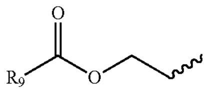 or 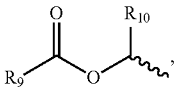, wherein $R_9$ and $R_{10}$ independently of each other are selected from linear or branched $C_1$-$C_6$-alkyl including-Me, -Et, —Pr, -iPr, -Bu, -iBu, -tBu, pentyl, neopentyl, or hexyl; notably $R_{10}$ is selected from H, -Me, -Et, -iPr;

$R_4$ is selected from H, —C(═O)—$C_1$-$C_6$-alkyl, wherein alkyl is linear or branched including —C(═O)-Me, —C(═O)-Et, —C(═O)—Pr, —C(═O)-iPr, —C(═O)—Bu, —C(═O)-tBu; —C(═O)-benzyl, polyethylenglycolyl (PEG), or a groups such as

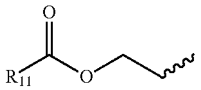 or 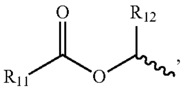, wherein $R_{11}$ and $R_{12}$ independently of each other are selected from linear or branched $C_1$-$C_6$-alkyl including-Me, -Et, —Pr, -iPr, -Bu, -iBu, -tBu, pentyl, neopentyl, or hexyl; notably $R_{12}$ is selected from H, -Me, -Et, -iPr, -iBu;

$R_6$, and $R_7$ are independently from each other selected from H, F, Cl, Br, I, aryl, linear or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1; and $C_{1-8}$ alkyl includes Me, Et, Pr, Bu, pentyl, hexyl, heptyl, octyl-alkyl being linear or branched.

or when $R_2$ is H, and $R_1$ and $R_5$ form a ring system, then said compound has formula III (formula III)

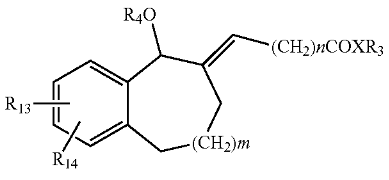

wherein n is 0 or 1;

X is O or NH m is 0 or 1;

$R_3$ is selected from H, linear or branched $C_1$-$C_6$-alkyl including -Me, -Et, —Pr, -iPr, -Bu, -iBu, -tBu, pentyl, neopentyl, hexyl, branched hexyl; benzyl, polyethylenglycolyl (PEG), or a group such as

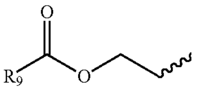 or 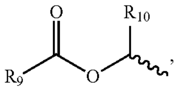, wherein $R_9$ and $R_{10}$ independently of each other are selected from linear or branched $C_1$-$C_6$-alkyl including-Me, -Et, —Pr, -iPr, -Bu, -iBu, -tBu, pentyl, neopentyl, or hexyl; notably $R_{10}$ is selected from H, -Me, -Et, -iPr;

$R_4$ is selected from H, —C(═O)—$C_1$-$C_6$-alkyl, wherein alkyl is linear or branched including —C(═O)-Me, —C(═O)-Et, —C(═O)—Pr, —C(═O)-iPr, —C(═O)—Bu, —C(═O)-tBu, —C(═O)-benzyl, polyethylenglycolyl (PEG), or a groups such as

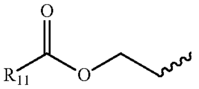 or 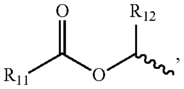, wherein $R_{11}$ and $R_{12}$ independently of each other are selected from linear or branched $C_1$-$C_6$-alkyl including-Me, -Et, —Pr, -iPr, -Bu, -iBu, -tBu, pentyl, neopentyl, or hexyl; notably $R_{12}$ is selected from H, -Me, -Et, -iPr;

$R_{13}$, and $R_{14}$ are independently from each other selected from H, F, Cl, Br, I, aryl, straight or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1; and $C_{1-8}$ alkyl includes Me, Et, Pr, Bu, pentyl, hexyl, heptyl, octyl-alkyl being linear or branched. or a pharmaceutically acceptable salt thereof;

with the proviso that the compound is not one of the following:

(A)

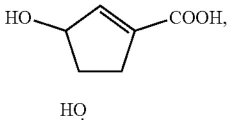, (B)

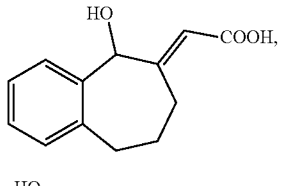, (C)

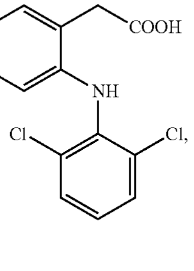,

-continued (D)

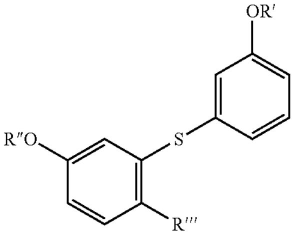

or

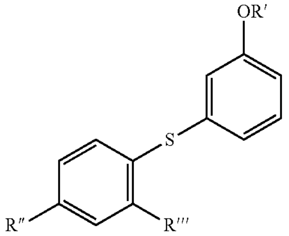

wherein R' is COOH, R" is H and R" is $OCH_3$, or wherein R' is COOH, R" is $CH_3$ and R'" is OH.

Within the scope of the present invention are isomers, tautomers, enantiomers, racemic forms or mixtures thereof and deuterated derivatives. Thus, eg compounds of formula I, which may be present in R or S forms, all such forms are included within the scope of the present invention as well as the racemic mixtures.

In the present context the term linear or branched $C_1$-$C_6$-alkyl includes methyl, ethyl, propyl, isopropyl, butyl, isobutyl, tert. butyl, pentyl, neopentyl and other branched pentyl hexyl and branched hexyl. The therm linear or branched $C_1$-$C_8$-alkyl included linear or branched $C_1$-$C_6$-alkyl as mentioned above and heptyl, branched heptyl, octyl and branched octyl.

Compounds of particular interest are those, wherein i) the compound has formula II or III, and wherein n is 0;
ii) the compound has formula IV, and n is 1;
iii) one of $R_3$ and $R_4$ is H;
iv) both $R_3$ and $R_4$ are H;
v) the compound has formula III, and $R_{13}$ is H and $R_{14}$ is in the 1 or 2 position;
vi) the compound has formula III, and $R_{13}$ is H and $R_{14}$ is selected from H, F, Cl, Br, I, aryl, straight or branched $C_{1-8}$ alkyl, $—CH_2(CH_2)_p$-aryl, or —CH═CH-aryl;
vii) the compound has formula III, and $R_{13}$ is H and $R_{14}$ is selected from H, F, Cl, Br, I, Ph, or —CH═CH-aryl;
viii) the compound has formula III, wherein $R_{13}$ is H and $R_{14}$ is selected from H, F, CI, Br, I, Ph, or —CH═CH-phenyl;
ix) $R_3$ is selected from

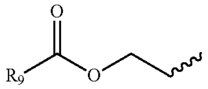

or

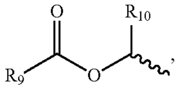

, or $R_4$ is selected from

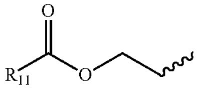

or

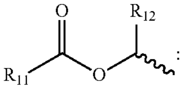

:

x) $R_3$ is

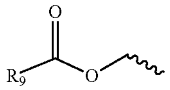

xi) the compound has formula II, and $R_4$ is H and $R_3$ is

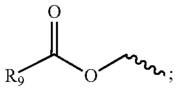

;

xii) the compound has formula Ill, wherein n=0, $R_3$ is H, X is O, $R_4$ is H and $R_{13}$ is selected from H, halogen, phenyl, methyl and $R_{13}$ is either in position 1 or in position 2 and $R_{14}$ is H.
xii) the compound has formula Ill, wherein n=0, $R_3$ is selected from H, -Me, -Et, —Pr, -iPr, -Bu, -tBu and Ph; X is O, $R_4$ is H and $R_{13}$ is selected from H, halogen, phenyl, methyl and $R_{13}$ is either in position 1 or in position 2 and $R_{14}$ is H.
xvv) the compound has one of the following structures

| Compound No. | Structure | |
| --- | --- | --- |
| 1 | 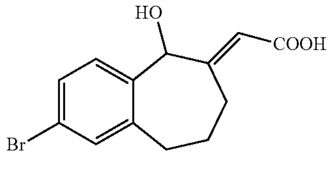 | Formula III |
| 2 | 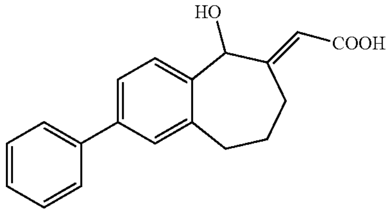 [SMILES: O=C(O)/C=C1\CCCc2cc(-c3ccccc3)ccc2C1O] | Formula III |

-continued
| Compound No. | Structure | |
|---|---|---|
| 3 | 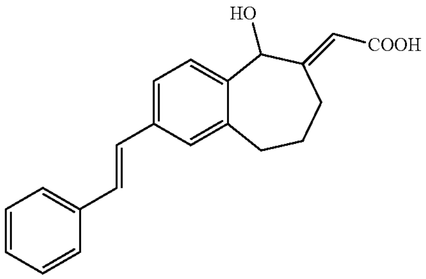 [SMILES: O=C(O)/C=C1\CCCc2cc(/C=C/c3ccccc3)ccc2C1O] | Formula III |
| 4 | 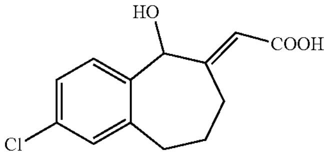 [SMILES: O=C(O)/C=C1\CCCc2cc(Cl)ccc2C1O] | Formula III |
| 5 | 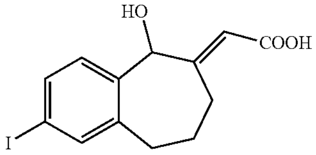 [SMILES: O=C(O)/C=C1\CCCc2cc(I)ccc2C1O] | Formula III |
| 6 | 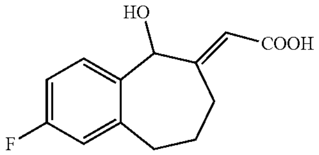 [SMILES: O=C(O)/C=C1\CCCc2cc(F)ccc2C1O] | Formula III |
| 7 | 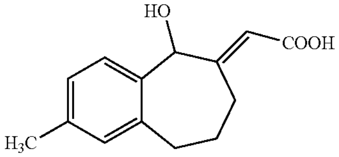 [SMILES: Cc1ccc2c(c1)CCC/C(=C\C(=O)O)C2O] | Formula III |
| 8 | 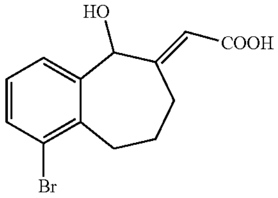 [SMILES: O=C(O)/C=C1\CCCc2c(Br)cccc2C1O] | Formula III |
| 9 | 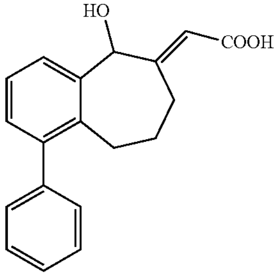 [SMILES: O=C(O)/C=C1\CCCc2c(-c3ccccc3)cccc2C1O] | Formula III |
| 10 | 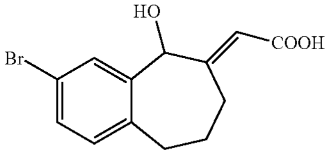 [SMILES: O=C(O)/C=C1\CCCc2ccc(Br)cc2C1O] | Formula III |

-continued
| Compound No. | Structure | |
|---|---|---|
| 11 | 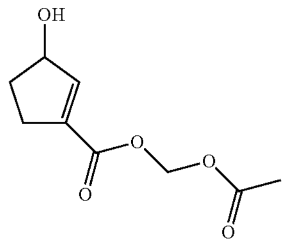 | Formula III |
| 12 | 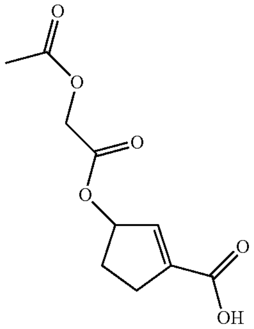 [SMILES: CC(=O)OCC(=O)OC1C=C(C(=O)O)CC1] | Formula II |
| 13 | 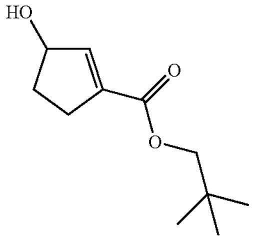 | Formula II |
| 14 | 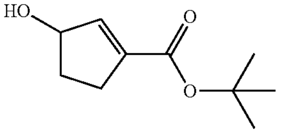 | Formula II |
| 15 | 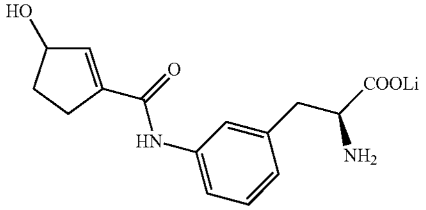 | Formula II - amide |
| A* | 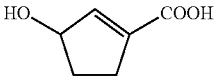 | Formula II |
| B* | 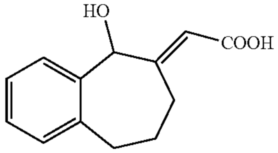 [SMILES: O=C(O)/C=C1\CCCc2ccccc2C1O] | Formula III |

-continued

| Compound No. | Structure | |
|---|---|---|
| C* | 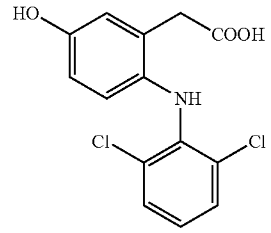 [SMILES: O=C(O)Cc1cc(O)ccc1Nc1c(Cl)cccc1Cl] | Formula IV |
| D* | 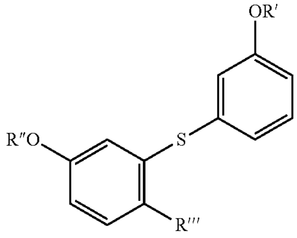 or 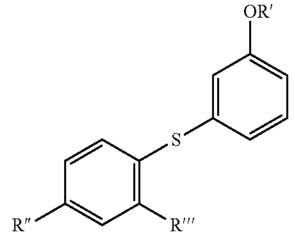 wherein R' is COOH, R" is H and R''' is $OCH_3$, or wherein R' is COOH, R" is $CH_3$ and R''' is OH. | |

*only medical use of these compounds are within the scope of the present invention.

The present invention also relates to a compound of formula (I) for use in medicine.

It necessary, the medical use is excluded for the compounds A, B, C, and/or D.

More specifically, the invention relates to a compound of formula (I) for use in the treatment of acute brain injury as defined herein.

The present invention discloses that 3-hydroxycyclopent-1-enecarboxylic acid (A), (Wellendorph et al., 2005), an in-house developed analogue of GHB, possesses neuroprotective properties against acute brain injury. It is contemplated that the compounds of formula (I) have similar neuroprotective properties. However, in contrast to GHB, A does not display any affinity for the $GABA_B$ binding site (Klein et al., 2016; Wellendorph et al., 2005), and so does not have the sedative effect that is problematic for GHB. A binds only to the 'elusive' high-affinity site. This binding site has been probed with a radiolabelled version of (E,RS)-6,7,8,9-tetrahydro-5-hydroxy-5H-benzocyclohept-6-ylidene acetic acid (NCS-382, B), termed $^3$H-B. More recently, the inventors have developed a radiolabelled version of A ($^3$H-A) (Vogensen et al, 2013), and using this, characterized and shown $^3$H-A binding to be restricted primarily to cortical and hippocampal brain regions in mice, rats and pigs (Klein et al., 2016). The inventors have shown that the sodium salt of A readily enters the brain after peripheral administration (Thiesen et al., 2015), and binds with specificity to the high-affinity target in vivo, with no apparent observations of acute toxicity or sedation in rodents after administration of doses as high as 500 mg/kg.

The present invention further discloses that (E)-2-(5-hydroxy-2-phenyl-5,7,8,9-tetrahydro-6H-benzo[7]annulen-6-ylidene)acetic acid (2), an in-house developed novel analogue of B, possesses neuroprotective properties against acute brain injury. The inventors have further shown that 2 and related analogues 1, 3-10 bind to the 'elusive' high-affinity site probed by $^3$H-A and $^3$H-B and passes cellular membranes.

The inventors have found that A affords a significant effect on minimizing the extent of cellular damage and improving functional recovery following stroke. Specifically, administration of A caused a decrease in infarct size and a dose-dependent improvement in motor function 3-7 days after the induction of the infarct. In the examples herein, A was administered 30 min, 3, 6 or 12 hrs after the induction of a focal stroke to the motor cortex. Surprisingly, and of crucial importance to the clinical use of A in the treatment of acute brain injury, A has a significant effect on both infarct size and motor performance even when given up to 12 hrs after the induction of the infarct. Similarly, 2 affords significant neuroprotection when administered peripherally as the sodium salt 3 or 6 hrs after induction of the injury.

The mechanism underlying the neuroprotective potential of A and 2 remains speculative. It is well-known that GHB reduces body temperature and decreases oxygen and glucose consumption in neurons. This mechanism has also proven useful as a post-stroke treatment in clinical studies. However, it should be noted that GABA modulators, such as clomethiazole, that have been reported to have a mild hypothermic response and afford significant protection, only delays, but does not prevent, the cascade of events that leads to cell death. This highlights the need to monitor drug-induced hypothermia and exclude drugs or receptor systems that are likely to induce such a response, such as $GABA_B$ receptors. GHB's control of body temperature has been shown to be mediated by $GABA_B$ receptors (Kaupmann et al., 2003), and unlike GHB, A does not bind to the $GABA_B$ receptor (Wellendorph et al., 2005). Consistent with this, the inventors show that A does not lower body temperature in mice at a high dose, highlighting that hypothermia is not involved in the neuroprotective activity of A. On the other hand, a decrease in the global central metabolic rate of glucose appears to be a non-$GABA_B$-mediated action. Compound 2 is contemplated to act by a similar mechanism given the ability to bind to the same high-affinity binding site.

A well-studied approach in drug development programs targeting stroke has been the use of immunomodulatory compounds. Accumulating evidence supports a linkage between activation of the proinflammatory response and infarct size. Likewise, a disruption of the blood-brain barrier (BBB) has been found to worsen the outcome following an ischemic stroke, possibly due to increased access for infiltrating lymphocytes and neutrophils. To investigate whether A could reduce these deleterious consequences of brain ischemia, the inventors looked at expression levels of selected inflammatory markers as well as the BBB disruptor, the extracellular proteinase MMP9, a well-known drug target in stroke research. Corroborating previous findings that MMP9 is heavily upregulated following stroke (12 and 72 hrs), the inventors observed that A significantly reduces this upregulation. Furthermore, when investigating the expression of inflammatory markers following ischemic stroke combined with A treatment, the inventors could confirm that the brain damage occurring during stroke drives a persistent inflammatory response, which A is able to dampen.

The present inventors have recently identified the molecular nature of the high-affinity binding site for GHB, A, B and GHB-related analogues, including the known compound 2-((2,6-dichlorophenyl)amino)-5-hydroxyphenylacetic acid (C) and the novel compounds 1 and 2 to be the calcium/calmodulin dependent protein kinase II alpha (CAMK2A). CAMK2A is a dodecameric enzyme and one of the most abundant proteins in the postsynaptic density (2-6% of total protein). CAMK2A is involved in a myriad of actions, including phosphorylation and regulation of synaptic activity, and plays a crucial role in long-term potentiation and memory formation. Moreover, CAMK2A protein expression is upregulated in the peri-infarct area following an ischemic stroke.

CAMK2A is known to phosphorylate both α-amino-3-hydroxy-5-methylisoxazole-4-propionic acid (AMPA) and NMDA receptors, and given that it is implicated in ischemic stroke, CAMK2A is rendered a promising drug target (Coultrap et al., 2011). Modulating CAMK2A activity directly in pre-clinical models of stroke and global cerebral ischemia, resulted in pronounced neuroprotective effects. The modulation of CAMK2A using the inhibitory peptide Tat-CN21 has shown promise in post-stroke treatment (Vest et al., 2007) and CN21 has been shown to prevent ischemia-induced increases in autophosphorylation of the Thr286 (pThr286) residue of the kinase (Ahmed et al. 2017). However, in addition to potential issues with stability and cell penetrance as well as bioavailability related to the general use of peptides, Tat-peptides are further known to cause hypertension. It is evident, that the modulation of CAMK2A as a target in brain ischemia is not trivial (Coultrap et al., 2011). For example, a complete ablation of CAMK2A in a knock-out mouse model appeared to exacerbate brain damage after an ischemic stroke (Waxham et al., 1996). The present inventors hypothesize that the mechanism of function from A arises from its direct interaction with and modulation of CAMK2A activity e.g. prevention of pThr286 autophosphorylation following ischemia as seen for CN21. However, data obtained by the inventors has shown that major differences exist between the binding site of A, 2 and CN21. Whilst CN21 is known to interact directly with the T-site of CAMK2A (Vest et al., 2007), compound A and related GHB analogues are contemplated to bind to either the kinase domain, the regulatory domain or the hub domain of CAMK2A. Given that no CAMK2A selective, small-molecule, non-peptide ligands exist, the presented compounds may also represent a novel mechanism of action.

The physico-chemical characteristics of A and related analogues, their fast absorption, entrance into the brain, and binding to the target, within minutes after intraperitoneal (i.p.) administration, make these small molecules vastly interesting. It is contemplated that the compounds of formula I, II, III and IV also have acceptable physico-chemical properties.

The inventors herein demonstrate that A and the novel analogue 2 display remarkable neuroprotective properties, and thus hold promise as candidates for diminishing neuronal death after acute brain injury.

Definitions

Acute Brain Injury

The term 'acute brain injury' as used herein refers to a primary cerebral or ischemic insult that damages brain tissue in an acute manner, but also initiates cascades of devastating neurotoxic effects. Examples include traumatic brain injury, stroke, subarachnoid haemorrhage, neonatal hypoxia-ischemia encephalopathy or associated in utero complications, haemodynamic shock with cardiac arrest, and global hypoperfusion during surgery or as a result from heart failure.

Compounds of the Invention (Also Denoted GHB-Related Analogue)

The term 'GHB-related analogue' as used herein refers to the compounds of the present invention that share a common GHB-related structure (formula I) and bind to a unique site in CAM K2A, for example A, B, C, 1, 2, or other compounds of the present invention.

Autophosphorylation

The term 'autophosphorylation' as used herein refers to the phosphorylation of CAMK2A on residues Thr286, Thr305 and Thr306.

CAMK2A

The term "CAMK2A" as used herein refers to Calcium/calmodulin-dependent protein kinase type II alpha.

Cerebral Metabolic Rate of Glucose (CMRglc)

The term 'CMRglc' as used herein refers to alterations in the cerebral glucose metabolism as measured by $^{14}C$-2-deoxyglucose autoradiography.

Haemorrhagic

The term 'haemorrhagic' as used herein refers to a stroke involving bleeding in or around the brain.

Ischemia

The term 'ischemia' as used herein refers to a disruption of blood supply to the tissue which limits delivery of oxygen and glucose.

Neuroprotective

The term 'neuroprotective' as used herein refers to the ability of a chemical substance to preserve nerve cell damage such as that induced by acute injury to the brain.

Peri-Infarct

The term 'peri-infarct' as used herein refers to the region surrounding the infarct.

Permanent Middle Cerebral Artery Occlusion (pMCAO) Focal Ischemia

The term 'pMCAO' as used herein refers to a permanent disruption of arterial blood flow to a region defined by the area supplied by the middle cerebral artery.

Photoaffinity Labelling

The term 'photoaffinity labelling' as used herein refers to a UV-light-induced activation of a chemical probe that covalently binds to its target upon such light stimulation.

Photothrombotic Focal Ischemia

The term 'photothrombotic focal ischemia' as used herein refers to method of introducing a cortical infarction through a photochemical reaction with a light-sensitive dye delivered by i.p. injection.

Recombinant

The term 'recombinant' as used herein refers to DNA sequences that have been transfected into and expressed as proteins in HEK293T cells.

Traumatic Brain Injury (TBI)

The term 'traumatic brain injury' as used herein refers to an acute damage to the brain which may lead to a disruption of the normal function of the brain.

FIGURE LEGENDS

FIG. 1: The GHB-related analogues A, B, C, 1-10 bind with nanomolar affinity to high-affinity forebrain binding sites using either A) $^{3}$H-B or B, C, D) $^{3}$H-A for radioactive labelling. The binding site does not recognize the known peptide CN21.

Figure 2:
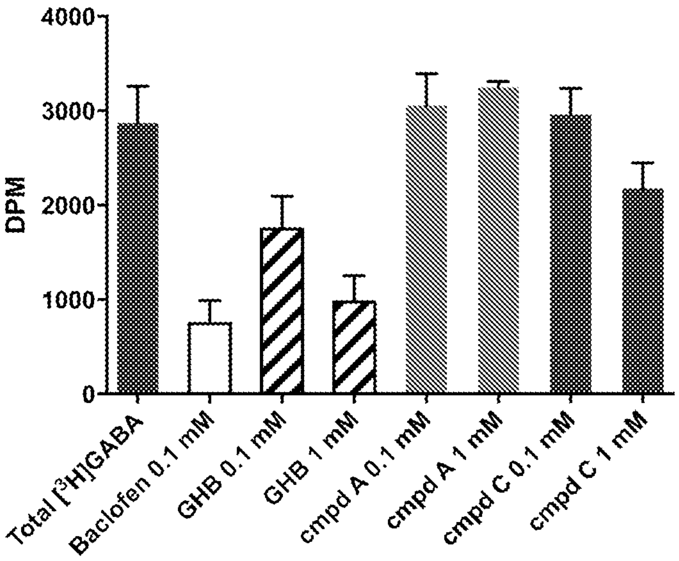

FIG. 2: Compound A does not bind to $GABA_B$ receptors whereas GHB does.

Figure 3:
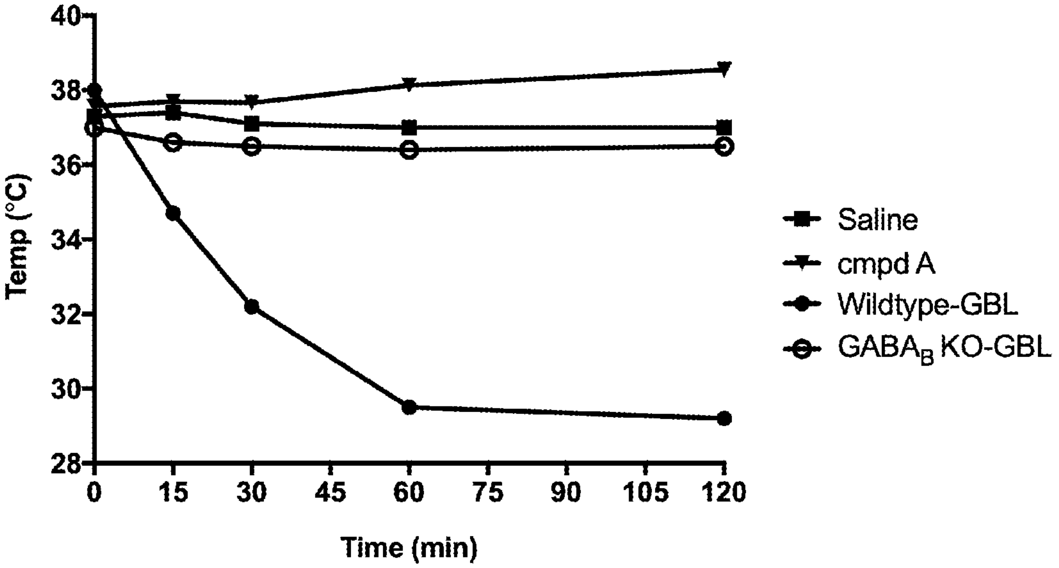

FIG. 3: Compound A does not produce $GABA_B$ receptor-mediated hypothermia in mice whereas GBL (GHB) does.

Figure 4:
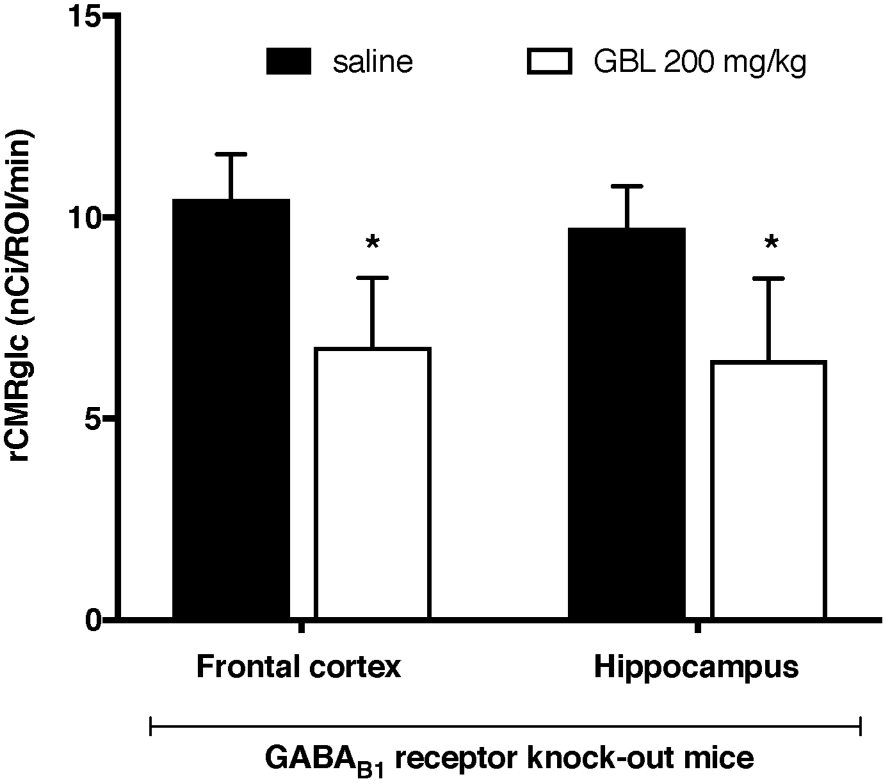

FIG. 4: The GHB prodrug GBL (200 mg/kg) produces a reduction in the cerebral glucose utilization not mediated by $GABA_B$ receptors.

Figure 5:
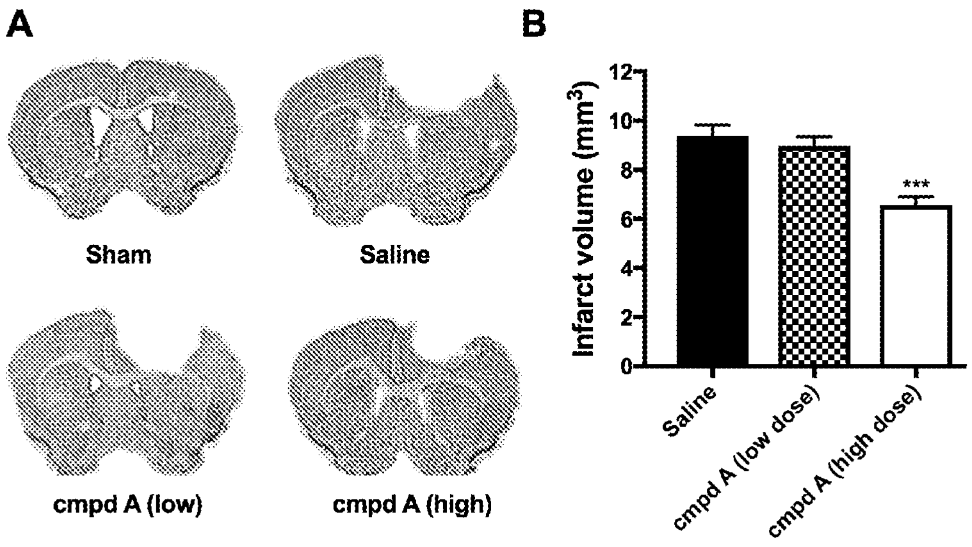

FIG. 5: Compound A (175 mg/kg) significantly reduces infarct size when administered (i.p.) 30 min to mice after photothrombotic focal ischemia induced 3 days earlier.

Figure 6:
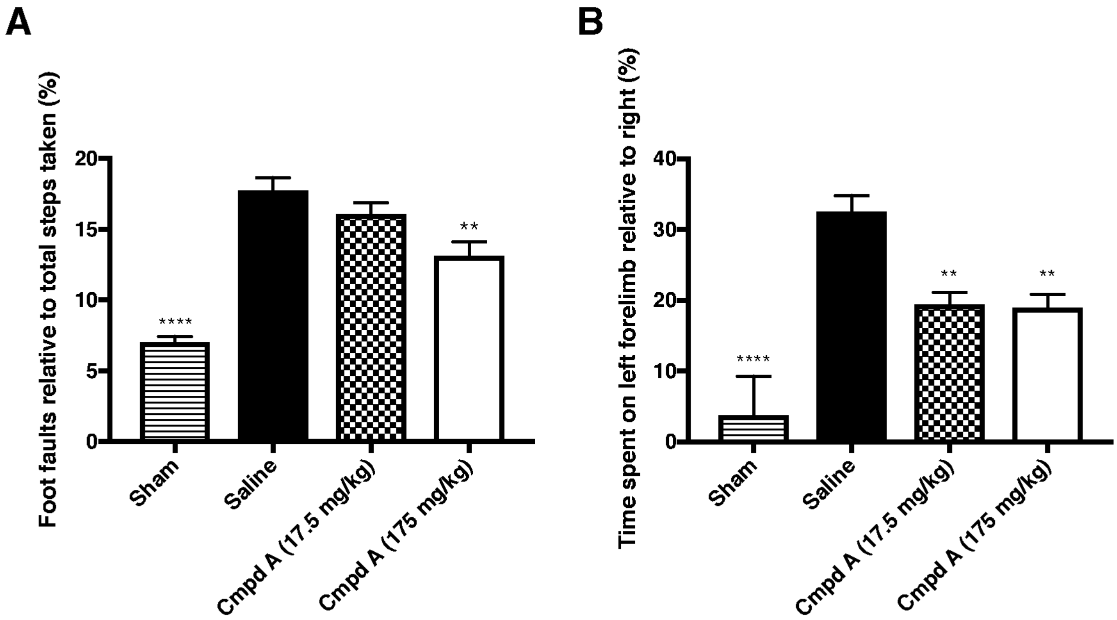

FIG. 6: Compound A (17.5 or 175 mg/kg) significantly improves motor performance in affected limbs in A) grid-walking or B) cylinder tasks when administered 30 min (i.p.) after photothrombotic focal ischemia induced 3 days earlier.

Figure 7:
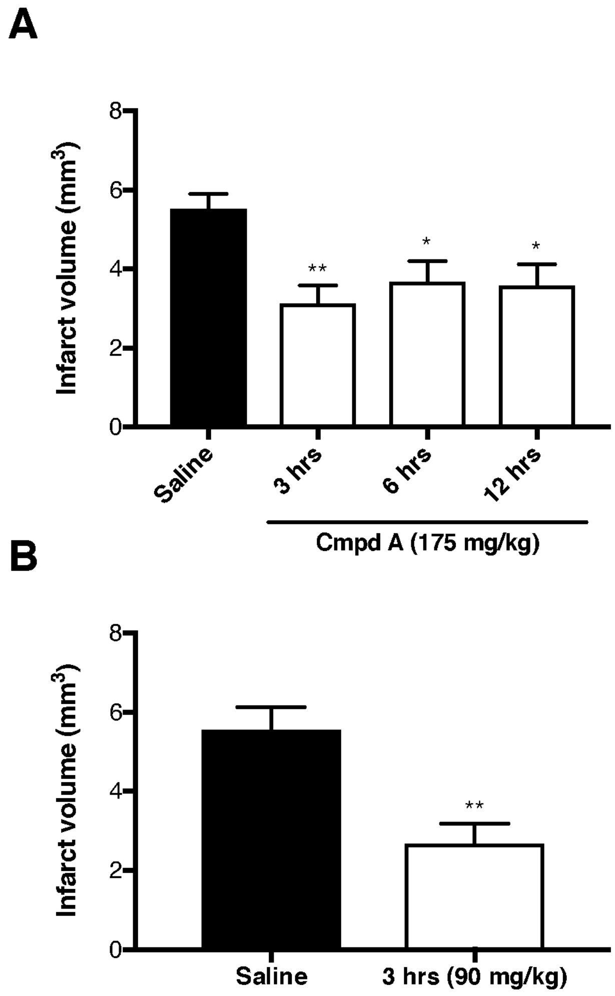

FIG. 7: Compound A (175 mg/kg) significantly reduces infarct size when administered (i.p.) to mice, either A) 3, 6 or 12 hrs after a photothrombotic focal insult produced 3 days earlier. B) A dose of 90 mg/kg is similarly neuroprotective.

Figure 8:
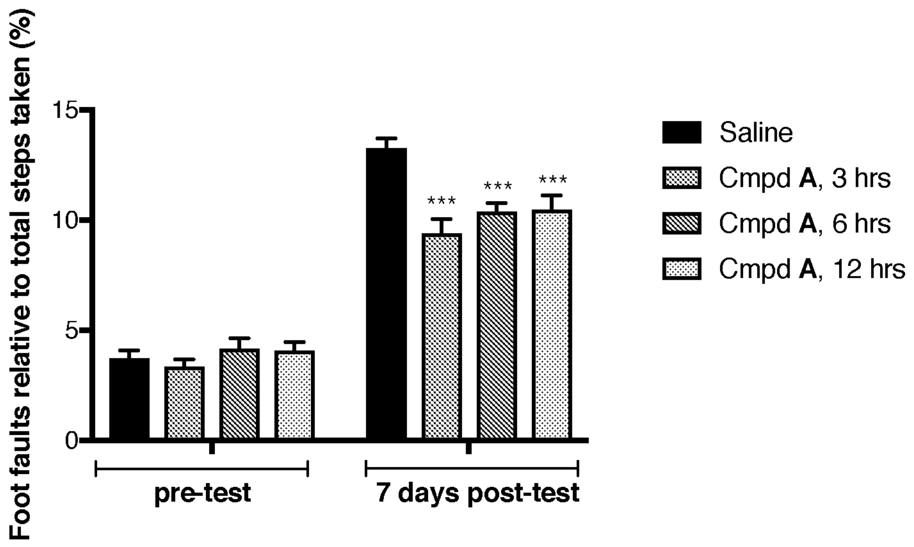
Figure 8:
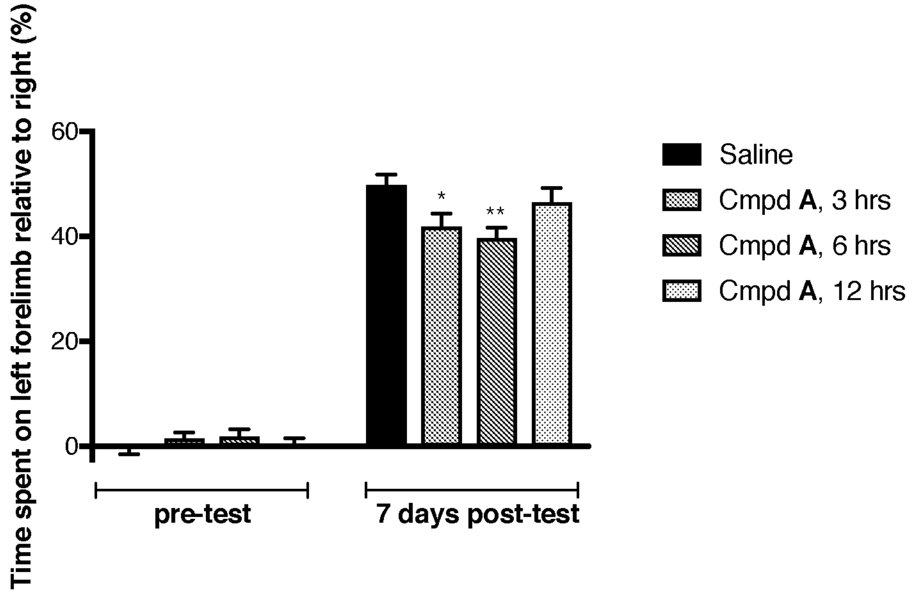

FIG. 8: Compound A (175 mg/kg) significantly improves motor performance in affected limbs in A) grid-walking or B) when administered 3, 6 or 12 hrs (i.p.) after a photothrombotic focal ischemia insult produced 3 days earlier.

Figure 9:
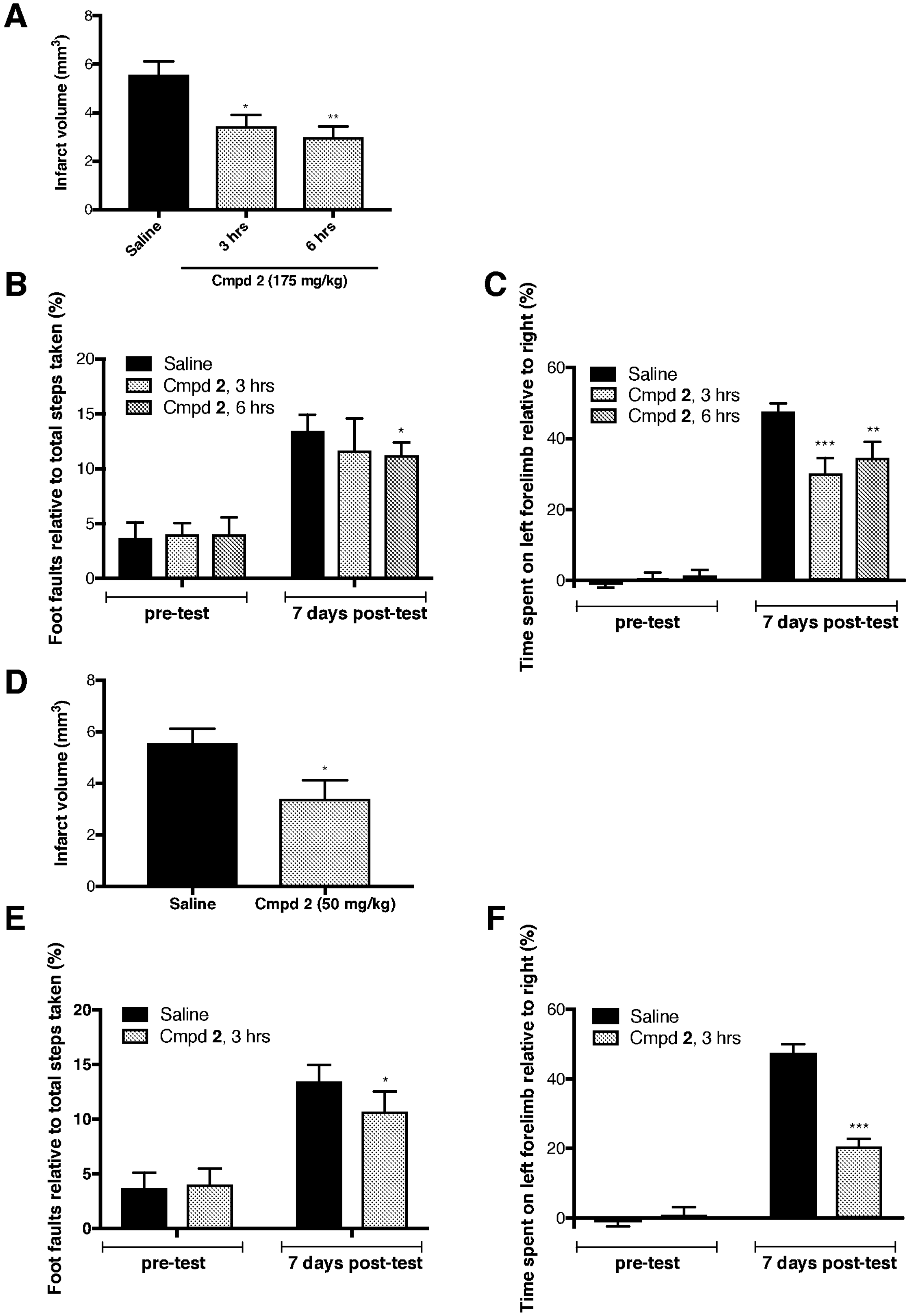

FIG. 9: Compound 2 significantly reduces infarct size when A) administered to mice (i.p.) 3 or 6 hrs (175 mg/kg) after a photothrombotic focal ischemia insult produced 7 days earlier, and B, C) significantly improves motor performance in both grid-walking and cylinder tasks measured at day 7 post-injury. D) Similarly at 50 mg/kg at 3 hrs, compound 2 reduces infarct size, and E, F) improves motor performance in both grid-walking and cylinder tasks measured at day 7 post-injury.

Figure 10:
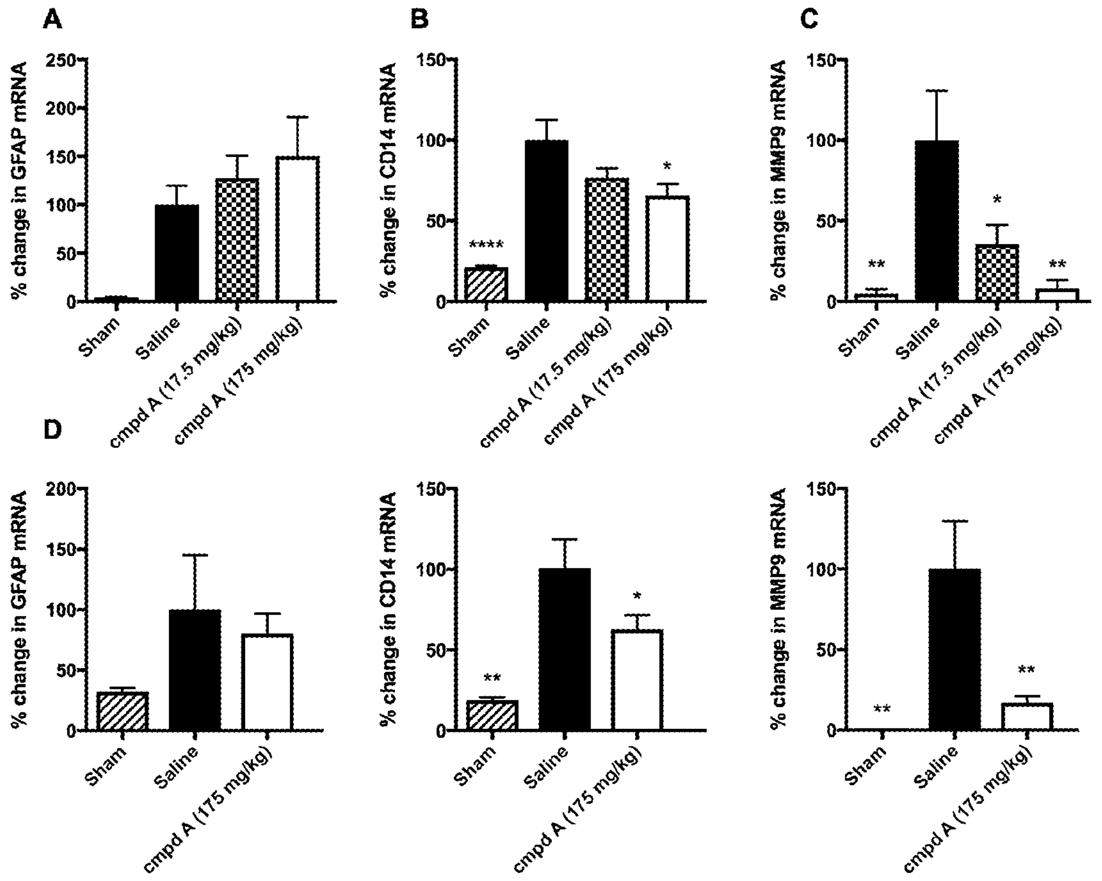

FIG. 10: Compound A significantly reduces the expression of the molecular markers CD14 and MMP9 when measured A, B, C) 3 days or D) 12 hrs after a photothrombotic focal insult.

Figure 11:
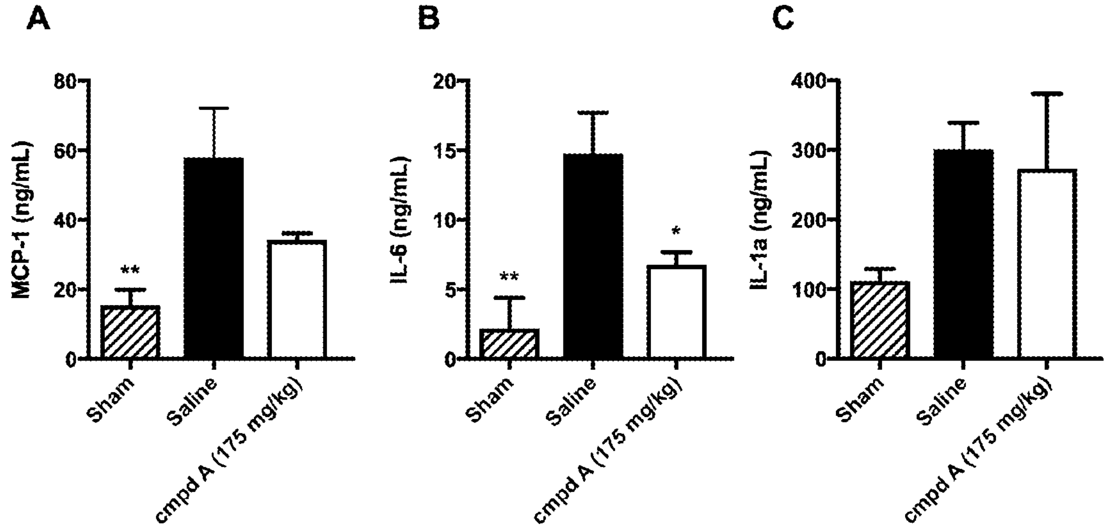

FIG. 11: Compound A significantly reduces plasma expression levels of the pro-inflammatory cytokine IL-6 when measured 4 hours after a photothrombotic focal insult.

Figure 12:
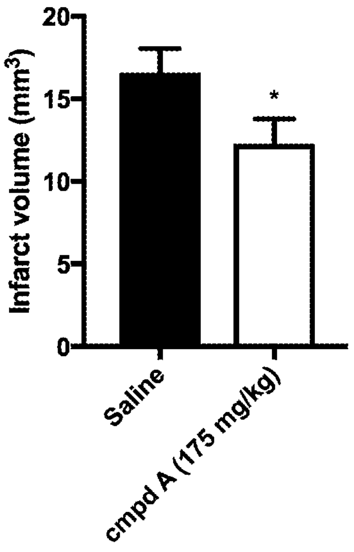

FIG. 12: Compound A (175 mg/kg) significantly reduces infarct size when administered (i.p.) to mice 30 min after a pMCAO focal lesion produced 3 days earlier.

Figure 13:
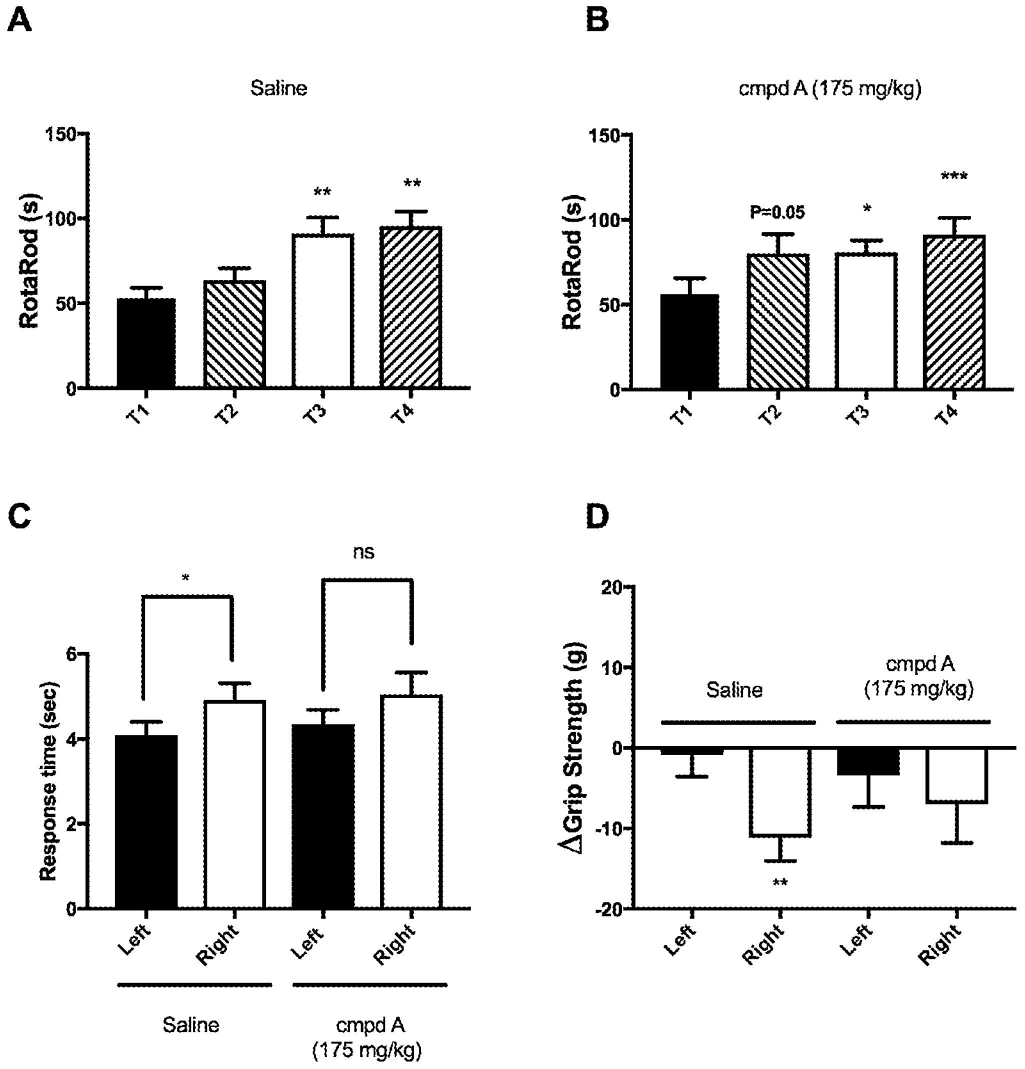

FIG. 13: Compound A (175 mg/kg) improves sensory-motor impairment when administered 30 min after a pMCAO focal lesion produced 2-3 days earlier. Effects were seen in A, B) rotarod, C) grip strength and D) Hargreaves tests.

Figure 14:
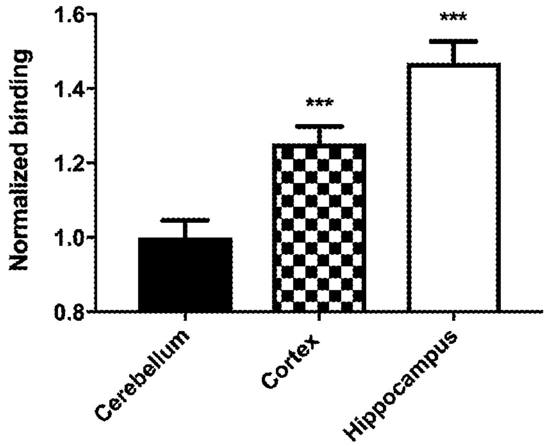

FIG. 14: $^{3}$H-A radioligand specific binding to forebrain regions confirms brain penetrance and target engagement of A. Mice were injected (i.p.) with radioligand (5 MBq per mouse) 30 min before the brain was dissected and subjected to autoradiography.

Figure 15:
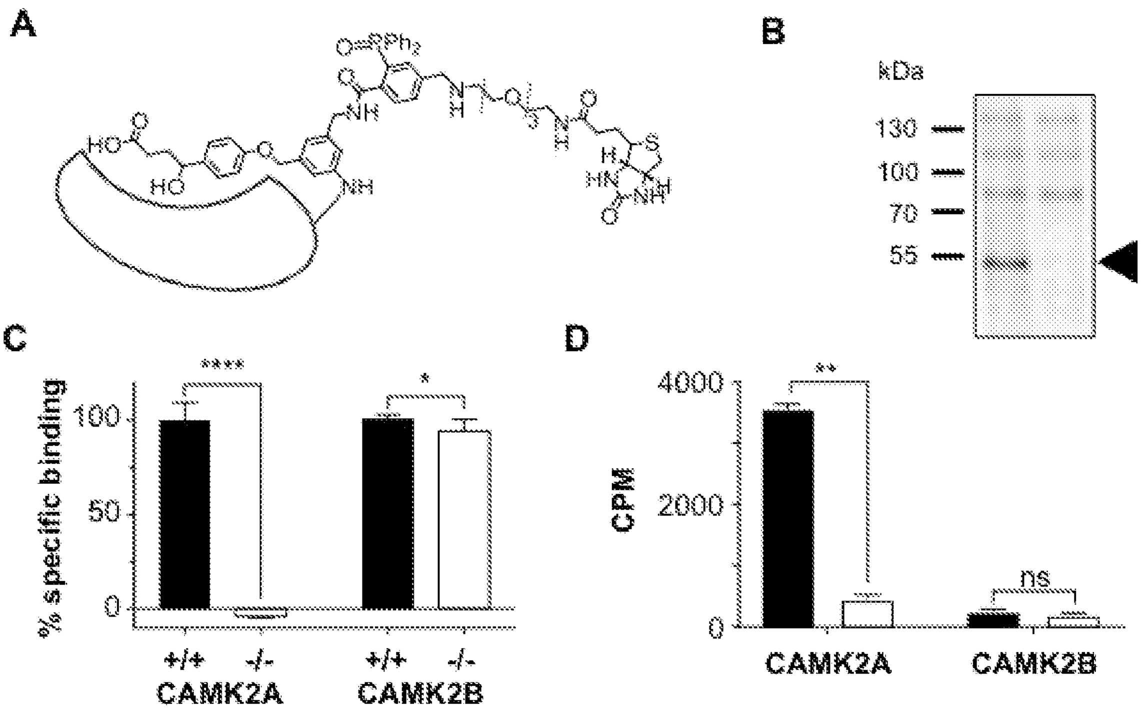

FIG. 15: CAMK2A is the high-affinity binding site for GHB in the mammalian brain, identified by A) photoaffinity labelling and proteomics, and validated by B) by Western blot and C, D) radioligand binding studies.

Figure 16:
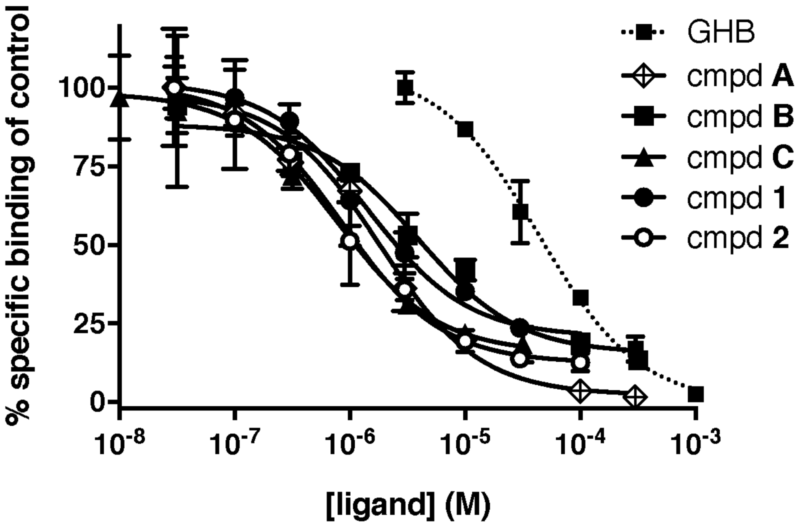

FIG. 16: GHB as well as the analogues A, B, C, 1 and 2 bind directly to recombinant CAMK2A expressed transiently in HEK293T cells.

Figure 17:
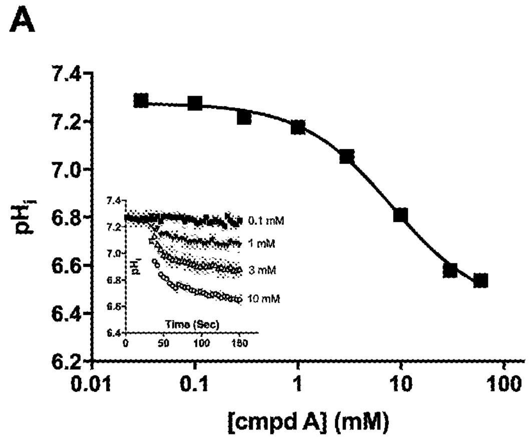
Figure 17:
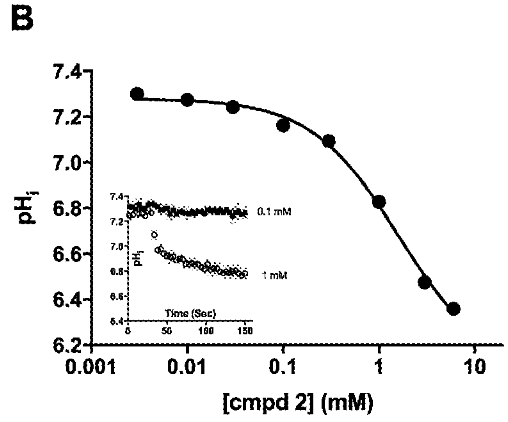

FIG. 17: The cellular uptake of compounds A and 2 is mediated by their substrate activity at proton-coupled transporters endogenously present in tsA201 cells.

Figure 18:
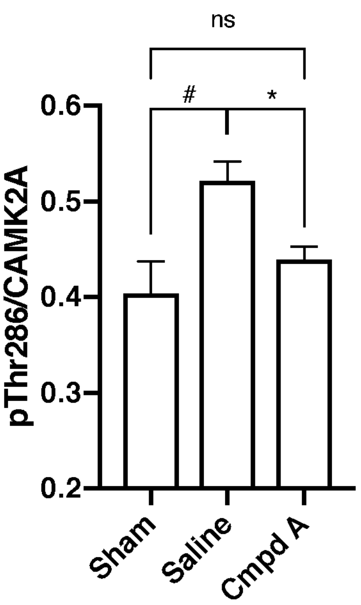

FIG. 18: Ex vivo pThr286 autophosphorylation assay on tissues from mice subjected to photothrombosis shows that compound A decreases excessive autophosphorylation.

EXAMPLES

Materials and Methods

Rat Brain Membrane Binding Assays

Compounds were evaluated in the $^{3}$H-A, $^{3}$H-B, or $^{3}$H-GABA binding assays (for $GABA_B$) according to previously published protocols using crude synaptic membranes prepared from rat cortex (Wellendorph et al., 2005 and Klein et al., 2016). For $^{3}$H-A and $^{3}$H-B binding, membranes were incubated with increasing concentrations of test compound or 1-10 mM GHB for non-specific binding in a 50 mM potassium phosphate buffer (pH 6.0 or pH 7.4) for 1 hr at 0-4° C. in 96-well ligand plates. Following incubation by rapid filtration through GF/C unifilters (PerkinElmer, Boston, MA, USA), using a 96-well Packard cell-harvester (PerkinElmer) and three fast washes with ice-cold binding buffer, microscint scintillation fluid (PerkinElmer) was added to the dried filters, and the amount of filter-bound radioactivity was quantified in a Packard TopCount microplate scintillation counter (PerkinElmer). For $GABA_B$ receptor binding assays, membranes were incubated with increasing concentrations of test compound or 100 μM baclofen (Sigma) for non-specific binding in a 50 mM Tris-HCl buffer (pH 7.4) containing 2.5 mM $CaCl_2$) and 40 μM isoguvacine (Sigma) for 1 hr at room temperature in 48-well setup. The binding reactions were terminated by rapid filtration through GF/C filters (Whatman), soaked in 0.1% polyethylene imine, using a Brandell 48-well harvester and rapid washing with ice-cold binding buffer. The dried filters were added Optifluor scintillation liquid (PerkinElmer) and counts determined on a Tricarb 4910 TR Scintillation counter (PerkinElmer). Data are presented as % specific binding (of control), and $IC_{50}$ or $K_i$ values calculated by means of non-linear regression curve-fitting and the Cheng-Prusoff equation, respectively.

Temperature Recording

Mice were pre-treated with saline injections (0.9% saline) i.p. for 4 days prior to the experiment to minimize stress on the day of the experiment. Experiments were conducted in a quiet room, in which mice were left undisturbed for at least two hrs prior to the experiment. After the i.p. injections, mice were left in their home cages for two hrs, had core body temperature recorded, and were then euthanized. The core body temperature was measured rectally by a thermometer (model DM 852; ELLAB Instruments; Copenhagen, Denmark) via a lubricated thermistor probe (model PRA-22002-A, 2.2 mm diameter; ELLAB Instruments). Mice were held at the base of the tail and measured until a stable temperature measurement was obtained.

Glucose Metabolism Studies

Regional cerebral metabolism rate of glucose (rCMRglc) was measured in conscious free-moving $GABA_{B(1)}$ receptor knock-out mice (Kaupmann et al., 2003) using a semiquantitative index of rCMRglc (irCMRglc) which avoids the need to perform blood sampling throughout the experiment. 10 min following GBL (200 mg/kg) or saline i.p. injections, mice were injected i.p. with 5 μCi of $^{14}C$-2-deoxyglucose (specific activity 54.1 mCi/mmol, Sigma, UK) dissolved in 0.4 ml saline. After 45 min, mice were euthanized by cervical dislocation and brains were snap-frozen and stored at −80° C. until sectioning. Coronal sections of 20 μm were collected at 2.68, 1.34, 0.74, −1.7, −3.08 and −5.68 mm corresponding to bregma, and were thaw-mounted onto glass slides (Fischer Scientific, Denmark). Autoradiographic images were produced by exposing sections to a $^{14}C$-sensitive plate (Science Imaging Scandinavia AB, Nacka, Sweden) in cassettes for five days with $^{14}C$-microscales (Amersham, UK). Finally, the imaging plate was scanned on a BAS-2500 scanner (Fujifilm Europe GmbH, Dusseldorf, Germany). Specific and non-specific binding in frontal cortex and hippocampus were calculated by measuring pixel density using ImageJ and converted to nCi using the calibration scale.

The Photothrombotic Mouse Model of Focal Ischemia

All procedures were performed in accordance with the guidelines on the care and use of laboratory animals set out by the University of Otago, Animal Research Committee and the Guide for Care and Use of Laboratory Animals (NIH Publication No. 85-23, 1996). All in vivo studies were approved by the University of Otago Animal Ethics Committee and are reported according to the ARRIVE (Animal Research: Reporting In Vivo Experiments) guidelines. The photochemical cortical lesion model resembles situations of acute brain injury related clinically to stroke and traumatic brain injury (TBI). Focal ischemia was induced by photothrombosis in male C57BL/6J mice (8-10 weeks) weighing ~23-30 g as previously described (Clarkson et al., 2010). Under anesthesia with isoflurane (2% to 2.5% in $O_2$) mice were placed in a stereotactic apparatus, the skull exposed through a midline incision, cleared of connective tissue and dried. A cold light source (KL1500 LCD, Zeiss, Auckland, New Zealand) attached to a 40× objective providing a 2-mm diameter illumination was positioned 1.5 mm lateral from bregma. Then, 0.2 ml of Rose Bengal (Sigma-Aldrich, Auckland, New Zealand; 10 mg/ml in normal saline) was administered i.p. After 5 min, the brain was illuminated through the exposed intact skull for 15 min, while keeping body temperature at 37.0±0.3° C. degrees using a heating pad (Harvard apparatus, Holliston, MA, USA). The skin was glued and animals left in a cage placed on a heating pad during the wake-up phase. Mice were housed under a 12-hr light/dark cycle with ad libitum access to food and water. Further, the mice were monitored and weighed on a daily basis.

Compound Sources and Preparation of Compounds for In Vivo Studies

The sodium salt of A was synthesized in-house as described previously (Vogensen et al., 2013). The sodium salt of GHB, the GHB prodrug γ-butyrolactone (GBL), NCS-382 (B), diclofenac and 4'-hydroxydiclofenac were purchased from Sigma-Aldrich, whereas C was obtained from Carbosynth or SantaCruz (Berkshire, UK). The CN21 peptide was obtained from Genscript.

For in vivo studies, all compounds were dissolved in a mixture of sterile saline and $H_2O$ to obtain isotonicity (0.9%) and administered as 10 mg/ml and 10 μl of solution per gram mouse body weight. The injection of compound (i.p.) was performed 30 min, 3, 6 or 12 hrs after induction of the photothrombotic stroke. The vehicle groups received a corresponding volume of saline (0.9%) at the same time points (30 min, 3, 6 or 12 hrs).

Behavioural Assessment in the Photothrombotic Model of Focal Ischemia

Forelimb motor performance was determined using the cylinder and grid-walking tasks as previously described (Clarkson et al., 2010). All animals were tested both in a pre- and post-testing session, 1 week before and 3 days or 7 days after the ischemic insult, respectively. Observers who scored the behaviour were blinded to the treatment groups.

The Permanent Middle Cerebral Artery Occlusion (pMCAO) Model of Focal Ischemia

The pMCAO study was performed using age-matched, young adult (7-8 weeks), male C57BL/6J mice (Taconic). Mice were housed in separate cages under diurnal lighting and given free access to food (1314 Altromin) and water. Mice were acclimatized for seven days prior to surgery in accordance with guidelines approved by the Danish Animal Ethical Committee.

Focal cerebral ischemia was made by permanent occlusion of the distal part of the left middle cerebral artery (MCA). Mice were anesthetized by injection of a mixture of Hypnorm (fentanyl citrate 0.315 mg/ml and fluanisone 10 mg/ml; Jansen-Cilag), Stesolid (5 mg/ml Diazepamum; Dumex) and distilled water (1:1:2; 0.20 ml/10 g body weight, s.c.). The mouse was placed on a 37±0.5° C. warm heating pad and a skin incision was made from eye to ear. The parotid gland and the upper part of the temporal muscle were pushed aside and a small hole was drilled over the distal part of the MCA. The MCA was occluded by electrocoagulation and the open incision was stitched with a 4.0 nylon-suture. After surgery, the mice were injected with 1 ml isotonic saline and their eyes were coated with ointment. The mice recovered from the surgery in a recovery room at 28° C. For treatment of post-surgical pain, mice were supplied s.c. with 0.15 ml Temgesic diluted 1:30 (stock: 0.3 mg/ml Buprenorphinum; Reckitt & Colman, UK) three times with an 8 hr interval starting immediately after surgery.

Behavioural Assessment in the pMCAO Model

To assess sensory-motor impairment, animals were tested in the rotarod, grip strength and Hargreaves tests 2-3 days post-stroke.

The rotarod (LE 8200, Panlab) measures motor performance in rodents by assessing the time during which the animal remains on a rotating rod. The rod rotation accelerates from 0 to 40 rounds per min (rpm) over a time period of 5 min 48 hrs post-stroke, mice were tested in four repeating trials with a 20 min interval (resting time). Prior to surgery, mice were pretrained to stay on the rod for 30 s at 4 rpm. The grip strength meter (BIO-GT-3, BIOSEB) allowed the study of neuromuscular functions in mice by determining the maximum force that is required to make the mouse release its grip.

The mouse is allowed to grasp a metal grid and then pulled backwards in the horizontal plane. The force applied to the grid is recorded as the peak tension. Individual (right and left) and total (both) front paw grip strength was measured before (baseline) and 3 days after pMCAO. Each mouse was tested in five sequential trials and the highest grip strength was recorded as the score. Thermal hyperalgesia (hind paw withdrawal from a normally innocuous heat source) was tested with a Hargreaves test setup. The latency times of five stimuli per hindlimb with at least 2 min break in between were recorded. The lowest and highest reflex latency scores were discarded and the average for left and right was calculated and plotted.

Statistical Analyses for In Vivo Studies

All analyses were performed in GraphPad 6.0 (San Diego, CA, USA). All data are presented as means+/−SEM. When comparing two groups, an unpaired t-test was used, and while comparing more than two groups, a one-way ANOVA with Holm-Sidak as post hoc test was performed. For the behavioural analyses, either two-way ANOVA with Bonferroni as post hoc test (photothrombotic ischemia data) or repeated-measures two-way ANOVA was used (pMCAO data).

Histological Assessment

For quantification of the infarcted area, animals were perfused with saline and then with 4% paraformaldehyde (PFA) and the brain dissected out and submerged in 4% PFA for post-fixing overnight. Then the brains were moved to 30% sucrose solution and kept at 4° C. until processing. Brains were cut in 30 μm sections, free-floating in antifreeze media. Sections were mounted, stained for cresyl violet and the infarct volumes determined by measuring every 6th section through the entire infarct as described in Lie et al (2017). All analyses were performed by an observer blinded to the treatment groups. Brains from the pMCAO studies were flash-frozen in $CO_2$ (gas) and processed into six parallel series of sections (30 μm). Separate series were collected on glass slides and used for infarct size analysis or in Eppendorf tubes and used for qPCR. The glass slides were stored at −80° C. until further processing, and then Cresyl-Violet stained and quantified as described for the photothrombotic photochemical method.

qPCR

Tissue from the peri-infarct area was collected and snap-frozen 12-72 hrs post stroke and RNA was extracted using a RNA mini kit (Qiagen) following the instructions from the manufacturer. Extracted RNA was treated with DNAse using Turbo DNA-free kit (Ambion), all according to the manufacturer's protocol. The reverse transcription was performed using gScript™ cDNA SuperMix (Quanta Biosciences, Gaithersburg, MD, USA) on a standard PCR machine (25° C. for 5 min, 42° C. for 30 min, 85° C. for 5 min) and cDNA stored at −20° C. until further processing.

qPCR was performed in 96-well plates (Agilent Technologies, Santa Clara, CA, USA) mixing PerfeCTa SYBR Green FastMix (Quanta Biosciences), nuclease free water (Qiagen, West Sussex, UK), and primers (TAG Copenhagen A/S (Copenhagen, Denmark). The PCR was performed with an initial denaturation step of 95° C. for 30 s, followed by 40 cycles of 5 s at 95° C., 60° C. for 15 s and 72° C. for 10 s. To assure single-product amplification, a dissociation curve analysis was performed consisting of 60 s at 95° C., 30 s at 55° C. and 30 s at 95° C. The qPCR was performed using the Agilent Mx3005P qPCR system (Agilent Technologies), and the corresponding MxPro software was used to determine the Ct values. The ΔCt values were calculated using 2 (Reference Ct−Target Ct).

| Primer sequences | | |
|---|---|---|
| SEQ ID NO 1 | CD14 (F) | AATCTACCGACCATGGAGC |
| SEQ ID NO 2 | CD14 (R) | ACTTTCCTCGTCTAGCTCG |
| SEQ ID NO 3 | IL-6 (F) | CTCTGGGAAATCGTGGAAAT |
| SEQ ID NO 4 | IL-6 (R) | CCAGTTTGGTAGCATCCATC |
| SEQ ID NO 5 | MMP9 (F) | CAGCCGACTTTTGTGGTCTTC |
| SEQ ID NO 6 | MMP9 (R) | CGGCCGTAGAGACTGCTTCTI |
| SEQ ID NO 7 | GFAP (F) | GGAGATGCGGGATGGTGAG |
| SEQ ID NO 8 | GFAP (R) | ACCACGTCCTTGTGCTCCTG |
| SEQ ID NO 9 | Rpl13a (F) | GGAGGGGCAGGTTCTGGTAT |
| SEQ ID NO 10 | Rpl13a (R) | TGTTGATGCCTTCACAGCGT |
| SEQ ID NO 11 | SDHA (F) | GCCCATGCCAGGGAAGATTA |
| SEQ ID NO 12 | SDHA (R) | TGTTCCCCAAACGGCTTCTT |

Quantification of Cytokines in Plasma

Detection of MCP-1 (monocyte chemotactant protein-1), IL-6 (interleukin-6) and IL-1a (interleukin-1a) was performed using a LEGENDplex assay kit according to the manufacturers' instructions (BioPlex, BioLegend, San Diego, CA, USA).

Photoaffinity Labelling and Enrichment of the GHB High-Affinity Binding Site from Rat Brain Crude synaptic membranes were incubated at a concentration of 0.125 mg/ml with 600 nM 4-(4-((3-azido-5-(azidomethyl)benzyl)oxy)phenyl)-4-hydroxybutanoic acid (SBV3) for 60 min at 4° C. in the dark. For the competition experiments, 0.1 nM-10 μM compound C was added. Membranes were then transferred on to non-tissue culture treated polystyrene plates and irradiated for 4 min at room temperature using a UVP Benchtop transilluminator set to high intensity (302 nm, 8 W, M-20V). Excess SBV3 was subsequently washed away with 1×PBS and centrifugation. For Staudinger Bertozzi ligation, the membranes were resuspended to a concentration of 0.5 mg/ml in 1×PBS and solubilized with 0.1% SDS and 1 mM EDTA for 15 min at 37° C. EZ-Link™ Phosphine-$PEG_3$-Biotin (ThermoFisher Scientific) was added to a final concentration of 200 μM and the reaction was shaken for 60 min at 37° C. Prior to streptavidin affinity enrichment, excess EZ-Link™ Phosphine-PEG3-Biotin was removed using PD MiniTrap G25 spin columns (GE Healthcare, Pittsburgh, PA, USA).

Biotinylated proteins were enriched using Pierce™ High Capacity Streptavidin Agarose (ThermoFisher Scientific). The solubilized membranes were diluted to a final concentration of 0.01% SDS and incubated with the resin under rotation for 30 min at room temperature. Enrichment was followed by a rigorous washing procedure (3×1 min with 10 CV 1×PBS, 0.01% Tween and 3×10 min with 10 CV 1×PBS, 0.01% Tween). Biotinylated proteins were eluted by boiling in 1× NuPAGE™ LDS sample buffer (ThermoFisher Scientific) supplemented with 100 μM DTT at 100° C. for 10 min under vigorous shaking. Eluates were loaded onto NuPAGE™ 4-12% Bis-Tris gels (ThermoFisher Scientific) and run for 50 min at 175 V. Gels were stained with GelCode™ Blue Stain (ThermoFisher Scientific) according to the manufacturer's instructions. Gel sections between the 70 kDa and 25 kDa marker (PageRuler™ Prestained Protein Ladder, 10 to 180 kDa, ThermoFisher Scientific) were cut out and diced into 1×1 mm cubes. In-gel digestions were carried out using 70 ng/band endoproteinase Lys-C(Sigma-Aldrich) over night at 37° C. and 175 ng/band trypsin (Sigma-Aldrich) for 8 h at 37° C. Peptide extracts were loaded onto in-house packed C18 STAGE Tips and eluted into a 96-well microtiter plate with 2×20 μl 40% acetonitrile, 0.5% acetic acid in water, followed by removal of organic solvents in a vacuum centrifuge and reconstitution of peptides in 2% acetonitrile, 0.5% acetic acid, 0.1% TFA in water.

Mass Spectrometry

All samples were analyzed on an Easy-nLC 1000 coupled to a Q-Exactive HF instrument (ThermoFisher Scientific) equipped with a nanoelectrospray source. Peptides were separated on a 15 cm analytical column (75 μm inner diameter) in-house packed with 1.9 μm C18 beads (Dr. Maisch, Germany). The column temperature was maintained at 40° C. using an integrated column oven (PRSO-V1, Sonation GmbH, Biberach, Germany). Peptides were separated by a linear gradient of increasing acetonitrile in 0.5% acetic acid for 35 min with a flow rate of 250 nl/min. The Q-Exactive HF mass spectrometer was operated in data-dependent acquisition mode. Spray voltage was set to 2 kV, S-lens RF level at 50, and heated capillary temperature at 275° C. All experiments were performed in the data-dependent acquisition mode to automatically isolate and fragment Top10 multiply-charged precursors according to their intensities. Former target ions were dynamically for 40 s excluded and all experiments were acquired using positive polarity mode. Full scan resolution was set to 60.000 at m/z 200 and the mass range was set to m/z 350-1400. Full scan ion target value was 3E6 allowing a maximum fill time of 100 ms. Higher-energy collisional dissociation (HCD) fragment scans was acquired with optimal setting for parallel acquisition using 1.3 m/z isolation width and normalized collision energy of 28. Target value for HCD fragment scans was set to 1e5 with a maximum fill time of 45 ms and analyzed with 60.000 resolution.

Raw LC-MS/MS data was processed using the MaxQuant software (v. 1.5.5.1) and searched against the rat and mouse UniProt databases (downloaded 13 Mar. 2017). In addition, the default contaminant protein database was included and any hits to this were excluded from further analysis. Carbamidomethylation of cysteine was specified as a fixed modification; phosphorylation of serine, threonine and tyrosine residues, oxidation of methionine, pyro-glutamate formation from glutamine and protein N-terminal acetylation were set as variable modifications.

Further data analysis was performed using Perseus (v. 1.5.6.0, Max-Planck Institute of Biochemistry, Department of Proteomics and Signal Transduction, Munich), Microsoft Office Exel and GraphPad Prism (v. 7.0). After database searching using MaxQuant, the proteingroups.txt file was processed using Perseus: Hits only identified by site or from the reverse database were excluded. Data were then exported to GraphPad Prism and non-linear regression was performed for all proteins using the "One site-Fit log $IC_{50}$" function. Best-fit values for Top and the $R^2$ values were plotted against each other to identify proteins with competitive dose-dependence behaviour.

$^3$H-A Binding to Recombinant CAMK2 Expressed in HEK293T Cells

HEK293T were cultured using standard conditions, using Dulbecco's modified Eagle Medium with GlutaMax, 10% fetal bovine serum and 1% penicillin-streptomycin, and incubated at 37° C. in a humidified atmosphere of 95% $O_2$ and 5% $CO_2$. Cells were transfected with rat CAMK2A (Origene construct RR201121) or rat CAMK2B (Origene construct RR200520) using PolyFect (Qiagen, West Sussex, UK) according to the manufacturer's protocol. Whole cell homogenates were prepared 48 hr post-transfection by washing the cells with ice-cold 1×PBS and harvesting by scraping. Cells were collected and centrifuged for 10 min at 1000×g. Cell pellets were resuspended in ice-cold 1×PBS and homogenized using 2×1 mm zirkonium beads in a bullet blender for 20 s at max speed (NextAdvance, NY, USA). Homogenates were cleared by centrifugation (10 min, 4° C., 14.000×g). Protein concentration was determined using the Bradford protein assay. 150-200 μg protein was incubated with 5 nM $^3$H-A and test compound in 1 ml total volume for 1 hr at 0-4° C. Nonspecific binding was determined with 1-10 mM GHB. Proteins were then precipitated by addition of ice-cold acetone (4× of the assay volume), vortexing and incubation at −20° C. for 1 hr. Proteins were filtrated rapidly through GF/C unifilters (Whatman) and washed. The dried filters were added scintillation liquid and radioactivity measured on a Tricarb 2100 Scintillation counter (Packard).

MCT-Mediated Uptake of GHB Analogues in tsA201 Cells

Uptake was measured using the cell-permeable pH-sensitive dye 2',7'-Bis(2-carboxyethyl)-5(6)-carboxyfluorescein acetoxymethyl ester (BCECF-AM) (Molecular Probes), utilizing the endogenous expression of MCTs in tsA201 cells. The day before the assay, cells were plated (50,000 cells/well) in black poly-D-lysin-coated 96-well plates with clear bottom (VWR, Radnor, PA, USA). On the day of assay, media was removed and cells loaded by addition of 50 μl BCECF AM/well (1.6 μM) in buffer (HBSS supplemented with 20 mM HEPES, 1 mM $CaCl_2$, 1 mM $MgCl_2$, and 1.8 mM probenecid, pH 7.4) and incubated for 45 min at 37° C., shielded from light. Cells were then washed twice with 100 μl buffer and the cell plate assayed at 37° C. in a FlexStation 3 reader (Molecular Devices). After ligand addition, the emitted fluorescence was recorded for 2 min at 538 nm after excitation of 485/444 nm. The fluorescence 485/444 nm was converted to intracellular pH by a nigericin calibration curve.

pThr286 Autophosphorylation in Dissected Mouse Tissues

Along with the standard protocol for photothrombotic focal ischemia, mice were treated with either saline or 175 mg/kg A (i.p.) 30 min after the injury. Three hours after the injury, mice were sacrificed, brains were dissected out and immediately submerged in ice-cold PBS supplemented with 1% phosphatase and protease inhibitors (Phosphatase inhibitor cocktail 3 #P0044 (Sigma), Phosphatase inhibitor cocktail 2 #P5726 (Sigma) and complete EDTA protease inhibitors (Roche) for 5 min. Cortex tissue from the infarct core region (i.e. 1.5 mm right of bregma including the primary motor cortex with a diameter of 2 mm) was dissected and snap-frozen on dry ice. Tissue homogenization was performed using 1×RIPA buffer supplemented with phosphatase and protease inhibitors and a Bullet Blender. Autophosphorylation was assessed by Western blot analysis, comparing the total level of CAMK2A (quantified using anti-CAMK2A, #NB100-1983, Novus Biologicals) to the level of phosphorylated CAMK2A (pThr286: #12716S, Cell Signalling Technology; goat anti-rabbit HRP: #PI-1000 X0126, Vector). Levels of pThr286 CAMK2A and CaMK2A were normalized to signals of a reference protein (anti-GAPDH, #NB300-221, Novus Biologicals). Subsequently, the ratio of the normalized signal of pThr286 CAMK2A and total CAMK2A expression was taken to detect changes in autophosphorylation. Digital images of bands were obtained with a cooled CCD-camera (FluorChem HD2 system, ProteinSimple) and densiometric analysis was performed with ImageStudioLite (LI-COR Biosciences).

Chemical Synthesis

Unless otherwise indicated, all reagents used in the examples below are obtained from commercial sources.

General Chemistry Methods

The compounds of the general formula IIIa may be prepared as given below from the appropriate substituted 6,7,8,9-tetrahydro-5H-benzo[7]annulen-5-on according to the procedures in Examples 1-3.

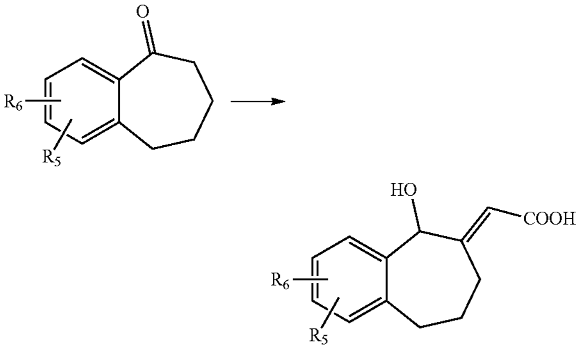

(formula IIIa)

The compounds of the general formula IVa may be prepared as given below from ethyl 2-(2-iodo-5-methoxyphenyl)acetate and an appropriate substituted aniline, phenol or thiophenol (X=N, O or S) catalyzed by copper in the presence of an inorganic base. The X=$CH_2$ may be prepared from ethyl 2-(2-iodo-5-methoxyphenyl)acetate using an appropriate substituted benzylhalide by a palladium catalyzed cross-coupling reaction. The protection groups may be cleaved by $BBr_3$.

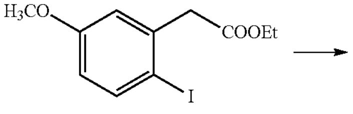

-continued

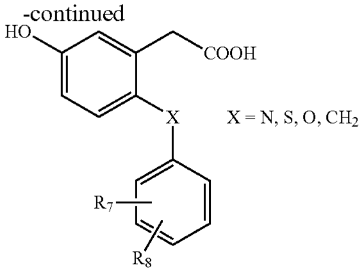

(formula IVa)

Example 1

Synthesis of (E)-2-(2-bromo-5-hydroxy-5,7,8,9-tetrahydro-6H-benzo[7]annulen-6-ylidene)acetic acid (1)

Step 1: To a solution of NaOH (368 mg, 9.1 mmol) in $H_2O$ (4.6 ml) and ethanol (10 ml) was added a mixture of 2-bromo-6,7,8,9-tetrahydro-5H-benzo[7]annulen-5-one (Murineddu et al., 2005) (400 mg, 1.6 mmol) and glyoxylic acid monohydrate (495 mg, 6.6 mmol) in water (10 ml) at room temperature. The mixture was stirred at room temperature until dissolution and then heated at reflux for 4 hr. After cooling, EtOH was removed in vacuo and the residual aqueous solution was washed with $Et_2O$ (2×15 ml) and the pH was adjusted to 1 with HCl and extracted with EtOAc (2×20 ml). The combined organic phases were dried over $MgSO_4$, filtered and evaporated. The residue was purified by column chromatography (DCM/MeOH 9.5:0.5+1% of AcOH) to give 369 mg, (75%) of (E)-2-(2-bromo-5-oxo-5,7,8,9-tetrahydro-6H-benzo[7]annulen-6-ylidene)acetic acid as a brown solid.

Step 2: Under a nitrogen atmosphere, $CeCl_3$ $7H_2O$ (231 mg, 0.6 mmol) and (E)-2-(2-bromo-5-oxo-5,7,8,9-tetrahydro-6H-benzo[7]annulen-6-ylidene)acetic acid (183 mg, 0.6 mmol) were dissolved in MeOH (30 ml). $NaBH_4$ (351 mg, 9.3 mmol) was slowly added to the solution at 0° C. The reaction was stirred at room temperature for 4 hr and then solvent was evaporated in vacuo. $H_2O$ (50 ml) was added to the residue and the pH was adjusted to 1 with HCl. The aqueous phase was extracted with DCM (3×30 ml), the combined organic phases were dried over $MgSO_4$, filtered and evaporated in vacuo. Purification by column chromatography (DCM+1% of AcOH) afforded (E)-2-(2-bromo-5-hydroxy-5,7,8,9-tetrahydro-6H-benzo[7]annulen-6-ylidene) acetic acid (120 mg, 65%) as a white solid. $^1H$ NMR (600 MHz, Methanol-$d_4$), δ: 7.39-7.36 (d, J=8.2 Hz, 1H), 7.35-7.32 (dd, J=8.2, 2.1 Hz, 1H), 7.26-7.25 (d, J=2.0 Hz, 1H), 6.00 (s, 1H), 5.25 (s, 1H), 3.50-3.45 (ddd, J=11.9, 6.9, 4.3 Hz, 1H), 3.07-3.00 (m, J=14.2, 9.1, 2.6 Hz, 1H), 2.81-2.71 (m, J=27.5, 13.1, 9.2, 3.5 Hz, 2H), 1.86-1.79 (m, J=13.7, 9.3, 7.0, 4.5, 2.5 Hz, 1H), 1.74-1.66 (m, J=13.6, 9.3, 4.4, 2.7 Hz, 1H). $^{13}$[C] NMR (151 MHz, Methanol-$d_4$), δ: 168.8, 162.4, 142.3, 140.3, 131.8, 129.0, 127.4, 120.5, 114.2, 76.3, 29.5, 29.3, 27.5.

Example 2

Synthesis of (E)-2-(5-hydroxy-2-phenyl-5,7,8,9-tetrahydro-6H-benzo[7]annulen-6-ylidene)acetic acid (2)

Step 1: Phenylboronic acid (101 mg, 0.8 mmol) and $K_2CO_3$ (173 mg, 1.2 mmol) were added to a solution of 2-bromo-6,7,8,9-tetrahydro-5H-benzo[7]annulen-5-one (Murineddu et al., 2005) (100 mg, 0.4 mmol) in DMF (16 ml) and $H_2O$ (8 ml). The solution was stirred under nitrogen atmosphere for 10 min, then tetrakis(triphenylphosphine) palladium (96 mg, 0.08 mmol) was added and the mixture was stirred under nitrogen atmosphere for additional 10 min. The reaction was heated at reflux for 24 hours. DMF was evaporated in vacuo before $H_2O$ (160 ml) was added and the aqueous phase was extracted with $Et_2O$ (80 ml). The organic phase was washed with $H_2O$ (160 ml) and brine (2×80 ml), dried over $MgSO_4$, filtered and evaporated in vacuo. Purification by column chromatography (Heptane/EtOAc 9:1) afforded 2-phenyl-6,7,8,9-tetrahydro-5H-benzo[7]annulen-5-one (65 mg, 68.8%) as a yellow oil.

Step 2: Performed as describe in example 1 (step 1) using NaOH (59 mg, 1.4 mmol) in $H_2O$ (0.7 ml) and ethanol (10 ml), 2-phenyl-6,7,8,9-tetrahydro-5H-benzo[7]annulen-5-one (65 mg, 0.2 mmol) and glyoxylic acid monohydrate (79 mg, 1.0 mmol) in $H_2O$ (5 ml). Purification by column chromatography (DCM/MeOH 9.5:0.5+1% of AcOH) afforded (E)-2-(5-oxo-2-phenyl-5,7,8,9-tetrahydro-6H-benzo[7]annulen-6-ylidene)acetic acid (47 mg, 59%) as a yellow solid.

Step 3: Performed as described in example 1 (step 2) using $CeCl_3$, $7H_2O$ (145 mg, 0.3 mmol), (E)-2-(5-oxo-2-phenyl-5,7,8,9-tetrahydro-6H-benzo[7]annulen-6-ylidene) acetic acid (116 mg, 0.3 mmol), MeOH (20 ml) and $NaBH_4$ (145 mg, 5.9 mmol). Purification by column chromatography (DCM+1% of AcOH) afforded (E)-2-(5-hydroxy-2-phenyl-5,7,8,9-tetrahydro-6H benzo[7]annulen-6-ylidene) acetic acid (92 mg, 80%) as a white solid. $^1H$ NMR (600 MHz, Methanol-$d_4$), δ: 7.61-7.56 (d, J=7.4 Hz, 2H), 7.53-7.50 (d, J=7.9 Hz, 1H), 7.47-7.42 (dd, J=7.9, 2.0 Hz, 2H), 7.42-7.37 (t, J=7.7 Hz, 1H), 7.35-7.33 (d, J=2.0 Hz, 1H), 7.32-7.27 (t, J=7.4 Hz, 1H), 6.03 (s, 1H), 5.33 (s, 1H), 3.55-3.39 (m, 1H), 3.24-3.04 (m, 1H), 2.96-2.73 (m, 2H), 1.91-1.67 (m, 2H). $^{13}$[C] NMR (151 MHz, Methanol-$d_4$), δ: 170.4, 164.1, 142.1, 141.8, 141.7, 141.2, 129.7, 129.3, 128.2, 127.9, 127.8, 126.1, 115.4, 78.5, 35.4, 30.8, 29.3.

Example 3

Synthesis of sodium (E)-2-(5-hydroxy-2-phenyl-5,7,8,9-tetrahydro-6H-benzo[7]annulen-6-ylidene)acetate (Sodium Salt of 2)

The sodium salt of 2 was prepared by dissolving 2 (85.4 mg, 0.290 mmol) in ethanol (2 ml) and NaOH (aq) (282 μl, 0.296 mmol, 0.5M Tritisol) was added. The solvent was removed in vacuo to give the product (90 mg, 99%) as white solid.

Example 4

Synthesis of (E)-2-(5-hydroxy-2-((E)-styryl)-5,7,8,9-tetrahydro-6H-benzo[7]annulen-6-ylidene)acetic acid (3)

Step 1: Styrene (8.4 ml, 6.0 mmol, 2 eq) and triethylamine (5.5 ml, 39.7 mmol, 19 eq) were added to a solution of 2-bromo-6,7,8,9-tetrahydro-5H-benzo[7]annulen-5-one (Murineddu et al., 2005) in $CH_3CN$ (15 ml). The solution was stirred under nitrogen atmosphere for 5 min, then tetrakis(triphenylphosphine)palladium (725 mg, 0.4 mmol) was added and the mixture was stirred under nitrogen atmosphere for an additional 5 min. The reaction was heated at reflux for 22 hrs sat. aq. $NH_4Cl$ (10 ml) was added, followed by extraction with EtOAc (2×20 ml). The combined organic phases were washed with $H_2O$ and brine, dried over $MgSO_4$ and evaporated in vacuo. Purification by column chromatography (Heptane/EtOAc 9.8:0.2) afforded (E)-2-styryl-6,7,8,9-tetrahydro-5H-benzo[7]annulen-5-one (229 mg, 52%) as a yellowish sticky oil.

Step 2: Performed as described in example 1 (step 1) using NaOH (152 mg, 10 mmol) in $H_2O$ (1.9 ml) and ethanol (7 ml), (E)-2-styryl-6,7,8,9-tetrahydro-5H-benzo[7]annulen-5-one (100 mg, 0.3 mmol) and glyoxylic acid monohydrate (140 mg, 5 mmol) in $H_2O$ (5 ml). Purification by column chromatography (DCM/MeOH 9.5:0.5+1% of AcOH) afforded (E)-2-(5-oxo-2-((E)-styryl)-5,7,8,9-tetrahydro-6H-benzo[7]annulen-6-ylidene)acetic acid (121 mg, 50%) as a yellow solid.

Step 3: Performed as described in example 1 (step 2) using $CeCl_3$, $7H_2O$ (70 mg, 0.1 mmol), (E)-2-(5-oxo-2-((E)-styryl)-5,7,8,9-tetrahydro-6H-benzo[7]annulen-6-ylidene) acetic acid (63 mg, 0.1 mmol), MeOH (20 ml) and $NaBH_4$ (74 mg, 1.9 mmol). Purification by column chromatography (DCM+1% of AcOH) afforded (E)-2-(5-hydroxy-2-((E)-styryl)-5,7,8,9-tetrahydro-6H-benzo[7]annulen-6-ylidene) acetic acid (30 mg, 49%) as a white solid. $^1H$ NMR (600 MHz, Methanol-$d_4$), δ: 7.55-7.50 (d, J=6.9 Hz, 2H), 7.45-7.37 (m, 2H), 7.36-7.30 (m, J=7.0 Hz, 2H), 7.30-7.27 (d, J=5.2 Hz, 1H), 7.25-7.19 (m, J=7.3, 6.8 Hz, 2H), 6.01 (s, 1H), 5.29 (s, 1H), 3.50-3.40 (m, 1H), 3.18-3.01 (m, J=14.1, 7.7, 3.4 Hz, 1H), 2.97-2.71 (m, 2H), 1.91-1.68 (m, 2H). $^{13}$[C] NMR (151 MHz, Methanol-$d_4$), δ: 170.6, 164.3, 141.6, 141.5, 138.8, 138.1, 129.6, 129.5, 129.3, 128.8, 127.7, 127.4, 125.7, 115.4, 78.6, 35.3, 30.7, 29.3.

Example 5

Synthesis of (E)-2-(2-chloro-5-hydroxy-5,7,8,9-tetrahydro-6H-benzo[7]annulen-6-ylidene)acetic acid (4)

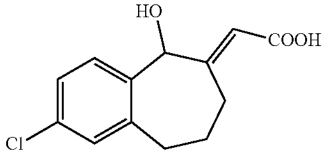 [SMILES: O=C(O)/C=C1\CCCc2cc(Cl)ccc2C1O]

Step 1: Performed as describe in example 1 (step 1) using NaOH (1.48 g, 37.1 mmol) in $H_2O$ (18 mL) and EtOH (40 mL), 2-chloro-6,7,8,9-tetrahydro-5H-benzo[7]annulen-5-one (Murineddu et al., 2005) (1.20 g, 6.18 mmol) and glyoxylic acid monohydrate (2.28 g, 24.7 mmol) in $H_2O$ (40 mL). Purification by column chromatography (DCM/MeOH 9.5:0.5+1% of AcOH) afforded (E)-2-(5-oxo-2-chloro-5,7,8,9-tetrahydro-6H-benzo[7]annulen-6-ylidene)acetic acid (764 mg, 49%) as a white solid.

Step 3: Performed as described in example 1 (step 2) using $CeCl_3$, $7H_2O$ (735 mg, 3.0 mmol), (E)-2-(5-oxo-2-chloro-5,7,8,9-tetrahydro-6H-benzo[7]annulen-6-ylidene) acetic acid (740 mg, 3.0 mmol), MeOH (150 mL) and $NaBH_4$ (1.1 g, 30 mmol). Purification by column chromatography (DCM+1% of AcOH) afforded (E)-2-(5-hydroxy-2-chloro-5,7,8,9-tetrahydro-6H-benzo[7]annulen-6-ylidene) acetic acid (402 mg, 52%) as a white solid. $^1H$ NMR (400 MHz, Methanol-$d_4$), δ: 7.44-7.43 (d, J=8.25 Hz, 1H), 7.20-1.18 (dd, J=2.29, 8.25 Hz, 2H), 7.11-7.10 (d, J=2.29 Hz, 1H), 6.00 (s, 1H), 5.27 (s, 1H), 3.49-3.45 (m, 1H), 3.07-3.02 (m, 1H), 2.81-2.73 (m, 2H), 1.86-1.80 (m, 1H), 1.74-1.68 (m, 1H). $^{13}$[C] NMR (151 MHz, Methanol-$d_4$), δ: 170.3, 164.0, 143.5, 141.2, 133.9, 130.3, 128.7, 127.4, 115.6, 77.8, 35.0, 30.9, 29.0

Example 6

Synthesis of (E)-2-(2-iodo-5-hydroxy-5,7,8,9-tetrahydro-6H-benzo[7]annulen-6-ylidene)acetic acid (5)

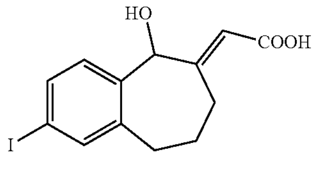 [SMILES: O=C(O)/C=C1\CCCc2cc(I)ccc2C1O]

Step 1: A mixture of 2-bromo-6,7,8,9-tetrahydro-5H-benzo[7]annulen-5-one (Murineddu et al., 2005) (826 mg, 3.5 mmol), bis(tributyltin) (4.0 g, 6.9 mmol) and tetrakis (triphenylphosphine)palladium (0) (400 mg, 0.3 mmol) in dry toluene (35 mL) was heated at reflux under argon atmosphere for 3 hours. The solvent was evaporated in vacuo to dryness. The crude product was carried on to step 2.

Step 2: A solution of 2-(tributylstannyl)-6,7,8,9-tetrahydro-5H-benzo[7]annulen-5-one (1068 g, 2.4 mmol) in THF (50 mL) was cooled to 0° C. and a solution of iodine (905 g, 3.6 mmol) in THF (35 mL) was drop wise added. After 1 hour at 0° C. the reaction was quenched by addition of saturated aqueous $Na_2S_2O_3$. Neutralized with a solution of saturated aqueous $NaHCO_3$ and extracted with EtOAc. The combined organic layers were dried over $Na_2SO_4$, filtered and evaporated in vacuo. Purification by column chromatography (heptane/EtOAc 4:1) afforded the product (272 mg, 27%) as a colorless oil. $^1$H NMR (400 MHz, $CDCl_3$), δ: 7.66 (dd, J=8.2, 1.7 Hz, 1H), 7.61 (d, J=1.7 Hz, 1H), 7.43 (d, J=8.1 Hz, 1H), 2.90-2.84 (t, J=7.2, 5.3 Hz, 2H), 2.75-2.68 (m, 2H), 1.93-1.75 (m, 4H). $^{13}$C NMR (100.6 MHz, $CDCl_3$), δ: 205.3, 143.2, 138.7, 138.3, 136.1, 130.3, 99.9, 40.9, 32.3, 25.2, 20.9.

Step 3: Performed as describe in example 1 (step 1) using NaOH (215.0 mg, 5.2 mmol) in $H_2O$ (3 mL) and EtOH (6 mL) and 2-iodo-6,7,8,9-tetrahydro-5H-benzo[7]annulen-5-one (272 mg, 0.95 mmol) and glyoxylic acid monohydrate (354 mg, 3.8 mmol) in $H_2O$ (7 mL). Purification by column chromatography (DCM/MeOH 9.5:0.5+1% of AcOH) afforded (E)-2-(5-oxo-2-iodo-5,7,8,9-tetrahydro-6H-benzo [7]annulen-6-ylidene)acetic acid (151 mg, 46%) as a yellow solid. $^1$H NMR (400 MHz, Methanol-$d_4$), δ: 7.77 (dd, J=8.1, 1.7 Hz, 1H), 7.72 (d, J=1.7 Hz, 1H), 7.47 (d, J=8.1 Hz, 1H), 6.68 (s, 1H), 2.82-2.76 (dt, J=6.8, 4.8 Hz, 4H), 2.07-1.98 (p, 2H). $^{13}$C NMR (100.6 MHz, Methanol-$d_4$), δ: 198.2, 169.3, 153.3, 143.7, 139.6, 137.6, 137.5, 131.7, 126.5, 102.0, 31.8, 26.2, 24.2.

Step 4: Performed as described in example 1 (step 2) using $CeCl_3$, $7H_2O$ (158 mg, 0.4 mmol), (E)-2-(5-oxo-2-iodo-5,7,8,9-tetrahydro-6H-benzo[7]annulen-6-ylidene) acetic acid (145 mg, 0.4 mmol), MeOH (20 mL) and $NaBH_4$ (160 mg, 4.2 mmol). Purification by column chromatography (DCM+1% of AcOH) afforded (E)-2-(2-iodo-5-hydroxy-5,7,8,9-tetrahydro-6H-benzo[7]annulen-6-ylidene) acetic acid (113 mg, 77%) as a white solid. $^1$H NMR (600 MHz, Methanol-$d_4$) δ: 7.55 (dd, J=8.1, 1.9 Hz, 1H), 7.46 (d, J=1.9 Hz, 1H), 7.23 (d, J=8.1 Hz, 1H), 5.99 (s, 1H), 5.24 (s, 1H), 3.50-3.45 (ddd, J=11.8, 6.9, 4.3 Hz, 1H), 3.04-2.98 (ddd, J=14.2, 9.1, 2.6 Hz, 1H), 2.80-2.71 (m, 2H), 1.86-1.79 (m, J=13.6, 6.9, 4.5, 2.5 Hz, 1H), 1.73-1.65 (m, J=13.5, 9.3, 4.3, 2.7 Hz, 1H). $^{13}$C NMR (151 MHz, Methanol-$d_4$), δ: 170.3, 163.8, 143.8, 142.4, 139.3, 136.8, 129.0, 115.7, 93.4, 77.8, 34.9, 30.9, 29.0. HPLC (254 nm): 100%.

Example 7

Synthesis of (E)-2-(2-fluoro-5-hydroxy-5,7,8,9-tetrahydro-6H-benzo[7]annulen-6-ylidene)acetic acid (6)

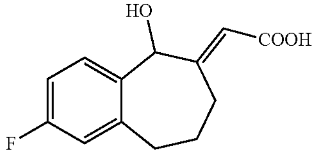

Step 1: To 2-(tributylstannyl)-6,7,8,9-tetrahydro-5H-benzo[7]annulen-5-one (1017 mg, 2.3 mmol) in acetone (35 mL) at room temperature were added $Ag_2O$ (31 mg, 0.1 mmol), $NaHCO_3$ (397 mg, 4.5 mmol) and F-TEDA-$BF_4$ (1204 mg, 3.4 mmol). The reaction mixture was stirred at reflux for 6 hours. After cooling to room temperature, the reaction mixture was filtered on a short pad of celite and evaporated in vacuo. The crude product was carried on to the next step.

Step 2: Performed as describe in example 1 (step 1) using NaOH (221 mg, 5.5 mmol) in $H_2O$ (8 mL) and EtOH (16 mL) and 2-fluoro-6,7,8,9-tetrahydro-5H-benzo[7]annulen-5-one (179 mg, 1.0 mmol) and glyoxylic acid monohydrate (370 mg, 4.0 mmol) in $H_2O$ (16 mL). Purification by column chromatography (DCM/MeOH 9.5:0.5+1% of AcOH) afforded (E)-2-(5-oxo-2-fluoro-5,7,8,9-tetrahydro-6H-benzo[7]annulen-6-ylidene)acetic acid. The crude product was carried on to the next step. MS (m/z) for $C_{13}H_{11}FO_3$ $(M-1)^-$ calcd.: 234.1, found: $(M)H^-$ 233.0.

Step 3: Performed as described in example 1 (step 2) using $CeCl_3$, $7H_2O$ (235.7 mg, 0.6 mmol), (E)-2-(5-oxo-2-fluoro-5,7,8,9-tetrahydro-6H-benzo[7]annulen-6-ylidene) acetic acid (135 mg, 0.6 mmol), MeOH (30 mL) and $NaBH_4$ (218 mg, 5.6 mmol). The crude product was purified by preparative HPLC to afford (E)-2-(2-fluor-5-hydroxy-5,7,8,9-tetrahydro-6H-benzo[7]annulen-6-ylidene)acetic acid (23.2 mg, 17%) as a white solid. $^1$H NMR (400 MHz, $CD_3OD$), δ: 7.44 (dd, J=8.5, 5.9 Hz, 1H), 6.89 (td, J=8.5, 2.7 Hz, 1H), 6.84 (dd, J=9.6, 2.7 Hz, 1H), 5.98 (s, 1H), 5.26 (s, 1H), 3.46-3.38 (ddd, J=12.1, 6.9, 4.7 Hz, 1H), 3.13-3.04 (ddd, J=14.2, 8.8, 3.4 Hz, 1H), 2.85-2.73 (m, 2H), 1.86-1.70 (m, 2H). $^{13}$C NMR (100.6 MHz, Methanol-$d_4$), δ: 170.4, 164.6, 164.1, 162.2, 144.1, 144.0, 138.3, 129.3, 129.2, 117.3, 117.1, 115.7, 113.7, 113.5, 78.1, 35.1, 30.6, 29.1. $^{19}$F NMR (376.4 MHz, Methanol-$d_4$), δ: −118.3 (s, 1F). MS (m/z) for $C_{13}H_{13}FO_3$ $(M-1)^-$ calcd.: 236.2, found: 235.0 $(M)H^-$. HPLC (254 nm): 95.5%.

Example 8

Synthesis of (E)-2-(2-methyl-5-hydroxy-5,7,8,9-tetrahydro-6H-benzo[7]annulen-6-ylidene)acetic acid (7)

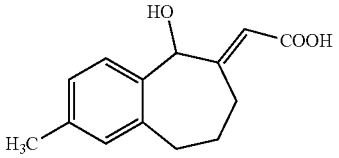 [SMILES: Cc1ccc2c(c1)CCC/C(=C\C(=O)O)C2O]

Step 1: Performed as describe in example 1 (step 1) using NaOH (6.71 g, 167.7 mmol) in $H_2O$ (80 mL) and EtOH (40 mL), 2-methyl-6,7,8,9-tetrahydro-5H-benzo[7]annulen-5-one (Murineddu et al., 2005) (4.84 g, 27.8 mmol) and glyoxylic acid monohydrate (10.28 g, 111.7 mmol) in $H_2O$ (40 mL). Purification by column chromatography (DCM/MeOH 9.5:0.5+1% of AcOH) afforded (E)-2-(2-methyl-5-oxo-5,7,8,9-tetrahydro-6H-benzo[7]annulen-6-ylidene)acetic acid (5.42 g, 85%) as a yellow solid. Step 2: Performed as described in example 1 (step 2) using $CeCl_3$, $7H_2O$ (6.35 g, 17.0 mmol), (E)-2-(2-methyl-5-oxo-5,7,8,9-tetrahydro-6H-benzo[7]annulen-6-ylidene)acetic acid (3.56 g, 15.5 mmol), MeOH (150 mL) and $NaBH_4$ (8.79 g, 232.3 mmol). Recrystallization from EtOAc after purification by column chromatography (DCM/MeOH 30:1+1% of AcOH) afforded (E)-2-(5-hydroxy-2-methyl-5,7,8,9-tetrahydro-6H-benzo[7]annulen-6-ylidene)acetic acid (1.56 g, 43%) as a white solid. $^1H$ NMR (400 MHz, Methanol-$d_4$), δ: 7.29 (d, J=7.7 Hz, 1H), 7.00 (dd, J=7.8, 1.9 Hz, 1H), 6.90 (s, 1H), 5.96 (s, 1H), 5.22 (s, 1H), 3.40-3.33 (m, 1H), 3.09-3.03 (m, 1H), 2.85-2.80 (m, 1H), 2.76-2.69 (m, 1H), 2.27 (s, 3H), 1.82-1.72 (m, 2H). $^{13}C$ NMR (101 MHz, Methanol-$d_4$) δ 170.4, 164.8, 141.2, 139.1, 138.4, 131.5, 128.1, 127.6, 115.3, 79.0, 35.2, 30.5, 29.4, 21.0. HPLC (254 nm): 100%. UPLC-MS: m/z=231.4 $[M-H]^-$ Example 9

Synthesis of (E)-2-(1-bromo-5-hydroxy-5,7,8,9-tetrahydro-6H-benzo[7]annulen-6-ylidene)acetic acid (8)

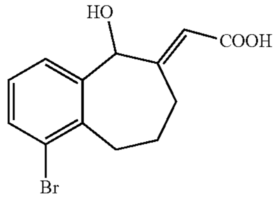 [SMILES: O=C(O)/C=C1\CCCc2c(Br)cccc2C1O]

Step 1: Performed as describe in example 1 (step 1) using NaOH (194 mg, 4.8 mmol) in $H_2O$ (3 mL) and EtOH (7 mL), 1-bromo-6,7,8,9-tetrahydro-5H-benzo[7]annulen-5-one (Gruber et al. 1983) (192 mg, 0.8 mmol) and glyoxylic acid monohydrate (299 mg, 3.2 mmol) in $H_2O$ (7 mL). Rough purification by column chromatography (DCM/MeOH 9.5:0.5+1% of AcOH) afforded crude (E)-2-(1-bromo-5-oxo-5,7,8,9-tetrahydro-6H-benzo[7]annulen-6-ylidene)acetic acid (172 mg, 73%) as a yellow solid.

Step 2: Performed as described in example 1 (step 2) using $CeCl_3$, $7H_2O$ (236 mg, 0.6 mmol), (E)-2-(1-bromo-5-oxo-5,7,8,9-tetrahydro-6H-benzo[7]annulen-6-ylidene) acetic acid (166 mg, 0.6 mmol), MeOH (8 mL) and $NaBH_4$ (214 mg, 5.6 mmol). Purification by preparative HPLC (gradient 30-55% B, eluent A ($H_2O$/TFA, 100:0.1) and eluent B (MeCN/$H_2O$/TFA, 90:10:0.1) at a flow rate of 20 mL $min^{-1}$, over 9 min) furnished (E)-2-(1-bromo-5-hydroxy-5,7,8,9-tetrahydro-6H-benzo[7]annulen-6-ylidene) acetic acid (92 mg, 55%) as white solid. $^1H$ NMR (400 MHz, Methanol-$d_4$) δ: 7.48 (d, J=8.7 Hz, 2H), 7.09 (t, J=7.8 Hz, 1H), 6.04 (s, 1H), 5.37 (s, 1H), 3.52-3.35 (m, 2H), 3.07-3.00 (m, 1H), 2.69-2.62 (m, 1H), 1.87-1.78 (m, 1H), 1.69-1.57 (m, 1H). $^{13}C$ NMR (101 MHz, Methanol-$d_4$) δ: 170.3, 163.8, 145.0, 139.9, 132.9, 129.0, 126.5, 125.5, 115.8, 77.5, 32.5, 30.8, 27.5. HPLC (254 nm): 98%. ESI-MS: m/z=295.0, 297.0 $[M-H]^-$ Example 10

Synthesis of (E)-2-(1-phenyl-5-hydroxy-5,7,8,9-tetrahydro-6H-benzo[7]annulen-6-ylidene)acetic acid (9)

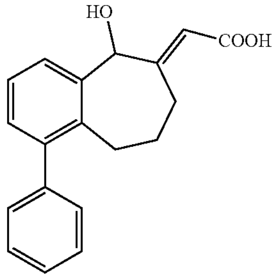 [SMILES: O=C(O)/C=C1\CCCc2c(-c3ccccc3)cccc2C1O]

Step 1: Performed as describe in example 2 (step 1) using phenylboronic acid (255 mg, 2.1 mmol), $K_2CO_3$ (436 mg, 3.1 mmol), 1-bromo-6,7,8,9-tetrahydro-5H-benzo[7]annulen-5-one (Gruber et al. 1983) ((247 mg, 1.0 mmol), tetrakis (triphenylphosphine)palladium (239 mg, 0.2 mmol) in DMF (24 mL) and $H_2O$ (16 mL). Rough purification by column chromatography (heptane/EtOAc 9:1) afforded crude 1-phenyl-6,7,8,9-tetrahydro-5H-benzo[7]annulen-5-one (220 mg, 90%) as a yellow oil.

Step 2: Performed as describe in example 1 (step 1) using NaOH (214 mg, 5.3 mmol) in $H_2O$ (3 mL) and EtOH (8 mL), 1-phenyl-6,7,8,9-tetrahydro-5H-benzo[7]annulen-5-one (210 mg, 0.9 mmol) and glyoxylic acid monohydrate (329 mg, 3.6 mmol) in $H_2O$ (5 mL). The crude (E)-2-(5-oxo-1-phenyl-5,7,8,9-tetrahydro-6H-benzo[7]annulen-6-ylidene)acetic acid was used for next step without any purification.

Step 3: Performed as described in example 1 (step 2) using $CeCl_3$, $7H_2O$ (362 mg, 1.0 mmol), (E)-2-(5-oxo-1-phenyl-5,7,8,9-tetrahydro-6H-benzo[7]annulen-6-ylidene) acetic acid (258 mg, 0.9 mmol), MeOH (14 mL) and $NaBH_4$ (338 mg, 8.9 mmol). Purification by preparative HPLC (gradient 30-72% B, eluent A ($H_2O$/TFA, 100:0.1) and eluent B (MeCN/$H_2O$/TFA, 90:10:0.1) at a flow rate of 20 mL $min^{-1}$, over 10 min) furnished (E)-2-(5-hydroxy-1-phenyl-5,7,8,9-tetrahydro-6H-benzo[7]annulen-6-ylidene) acetic acid (106 mg, 40% (overall yield in 2 steps)) as a white solid. $^1H$ NMR (600 MHz, Methanol-$d_4$) δ: 7.50 (dd, J=7.7, 1.4 Hz, 1H), 7.42-7.36 (m, 2H), 7.36-7.30 (m, 1H), 7.25-7.19 (m, 3H), 7.09 (dd, J=7.6, 1.4 Hz, 1H), 6.07 (s, 1H), 5.40 (s, 1H), 3.47 (ddd, J=12.5, 6.4, 4.6 Hz, 1H), 3.00 (ddd, J=14.5, 9.1, 2.7 Hz, 1H), 2.69 (tdd, J=11.6, 9.3, 3.7 Hz, 2H), 1.77-1.71 (m, 1H), 1.65-1.58 (m, 1H). $^{13}C$ NMR (151 MHz, Methanol-$d_4$) δ: 170.6, 164.5, 143.6, 143.4, 143.0, 138.3, 130.4, 130.3, 129.1, 127.9, 127.0, 126.3, 115.3, 78.1, 30.9, 29.6, 28.9. HPLC (254 nm): 100%. UPLC-MS: m/z=293.0 $[M-H]^-$ Example 11

Synthesis of (E)-2-(3-bromo-5-hydroxy-5,7,8,9-tetrahydro-6H-benzo[7]annulen-6-ylidene)acetic acid (10)

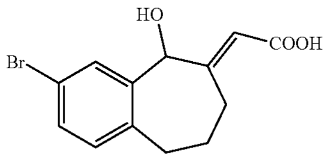 [SMILES: O=C(O)/C=C1\CCCc2ccc(Br)cc2C1O]

Step 1: Performed as describe in example 1 (step 1) using NaOH (246 mg, 6.0 mmol) in $H_2O$ (3 mL) and EtOH (7 mL), 3-bromo-6,7,8,9-tetrahydro-5H-benzo[7]annulen-5-one (Gruber et al. 1983) (237 mg, 1.0 mmol) and glyoxylic acid monohydrate (366 mg, 4.0 mmol) in $H_2O$ (7 mL). Purification by column chromatography (DCM/MeOH 9.5:0.5+1% of AcOH) afforded (E)-2-(3-bromo-5-oxo-5,7,8,9-tetrahydro-6H-benzo[7]annulen-6-ylidene)acetic acid (259 mg, 89%) as a yellow solid.

Step 2: Performed as described in example 1 (step 2) using $CeCl_3$, $7H_2O$ (356 mg, 1.0 mmol), (E)-2-(3-bromo-5-oxo-5,7,8,9-tetrahydro-6H-benzo[7]annulen-6-ylidene) acetic acid (256 mg, 0.9 mmol), MeOH (10 mL) and $NaBH_4$ (332 mg, 8.7 mmol). Purification by preparative HPLC (gradient 30-55% B, eluent A ($H_2O$/TFA, 100:0.1) and eluent B (MeCN/$H_2O$/TFA, 90:10:0.1) at a flow rate of 20 mL $min^{-1}$, over 9 min) furnished (E)-2-(3-bromo-5-hydroxy-5,7,8,9-tetrahydro-6H-benzo[7]annulen-6-ylidene) acetic acid (139 mg, 54%) as white solid. $^1H$ NMR (600 MHz, Methanol-$d_4$) δ: 7.64 (d, J=2.2 Hz, 1H), 7.28 (dd, J=8.0, 2.2 Hz, 1H), 7.00 (d, J=8.0 Hz, 1H), 6.01 (s, 1H), 5.28 (s, 1H), 3.57 (ddd, J=12.6, 6.5, 4.2 Hz, 1H), 2.99 (ddd, J=14.3, 8.6, 2.6 Hz, 1H), 2.80 (ddd, J=14.3, 9.8, 2.5 Hz, 1H), 2.66 (ddd, J=12.5, 9.9, 4.5 Hz, 1H), 1.90-1.84 (m, 1H), 1.65-1.59 (m, 1H). $^{13}C$ NMR (151 MHz, Methanol-$d_4$) δ: 170.3, 163.8, 145.0, 140.3, 132.4, 131.2, 129.3, 121.2, 115.6, 77.0, 34.9, 31.5, 29.0. HPLC (254 nm): 99%. ESI-MS: m/z=295.0, 297.0 $[M-H]^-$ Example 12

Synthesis of acetoxymethyl 3-hydroxycyclopent-1-ene-1-carboxylate (11)

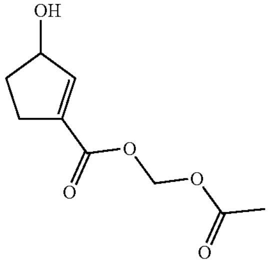

A mixture of 3-hydroxycyclopent-1-ene-1-carboxylic acid (A) (Vogensen et al., 2013) (207.4 mg, 1.62 mmol), $K_2CO_3$ (114.9 mg, 0.83 mmol) and KI (138.4 mg, 0.83 mmol) in dry DMF (5 ml) was stirred at room temperature for 30 min. To the reaction mixture, a solution of chloromethyl acetate (218.9 mg, 2.03 mmol) was added dropwise, and then stirred at 70° C. for 2 hrs before it was cooled to room temperature. Water (15 ml) was added, and aqueous phase was extracted with EtOAc (3×20 ml). The combined organic phase was dried over $MgSO_4$, filtered, and evaporated in vacuo. Purification by column chromatography (EtOAc/Heptane 1:1) furnished the product (202.5 g, 63%) as a transparent oil. $^1H$ NMR (600 MHz, Methanol-$d_4$) δ: 6.74 (q, J=2.1 Hz, 1H), 5.81 (s, 2H), 4.91-4.88 (m, 1H), 2.72-2.65 (m, 1H), 2.50-2.43 (m, 1H), 2.38-2.33 (m, 1H), 2.08 (s, 3H), 1.79-1.73 (m, 1H). $^{13}C$ NMR (151 MHz, Methanol-$d_4$) δ: 171.1, 164.9, 146.7, 138.3, 80.6, 77.5, 34.0, 30.6, 20.5. HPLC (254 nm): 96%.

Example 13

Synthesis of 3-(2-acetoxyacetoxy)cyclopent-1-ene-1-carboxylic acid (12)

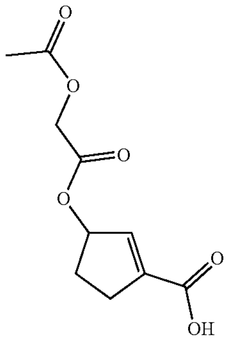 [SMILES: CC(=O)OCC(=O)OC1C=C(C(=O)O)CC1]

A mixture of acetoxyacetyl chloride (0.4 mL, 3.8 mmol) and acetoxyacetic acid (457 mg, 3.9 mmol) in THF (3 mL) was cooled to 0° C. N,N-Diisopropylethylamine (1.8 mL, 10.4 mmol) was added at less than 5° C. The resulting solution was warmed to room temperature and stirred for 30 min. 3-Hydroxycyclopent-1-ene-1-carboxylic acid (HOCPCA) (Vogensen et al., 2013) (222 mg, 1.7 mmol) and 4-dimethylaminopyridine (22 mg, 0.2 mmol) were dissolved in THF (1.5 mL). The solution was added to the reaction mixture in one portion and was stirred for 3 h at room temperature. Water (3 mL) was added and the reaction was stirred for 90 minutes at room temperature. The mixture was extracted with EtOAc. The combined organic phase was dried over $Na_2SO_4$, filtered, and evaporated in vacuo. Purification by column chromatography (EtOAc/heptane 1:1+1% of AcOH) furnished 3-(2-acetoxyacetoxy)cyclopent-1-ene-1-carboxylic acid (35 mg, 9%) as a off-white solid. $^1H$ NMR (600 MHz, Methanol-$d_4$) δ: 6.62 (q, J=2.1 Hz, 1H), 5.85-5.82 (m, 1H), 4.62 (s, 2H), 2.73-2.67 (m, 1H), 2.57-2.51 (m, 1H), 2.48-2.42 (m, 1H), 2.12 (s, 3H), 1.98-1.92 (m, 1H). $^{13}C$ NMR (151 MHz, Methanol-$d_4$) δ 172.1, 169.3, 167.7, 143.7, 139.0, 81.9, 61.9, 31.0, 31.0, 20.3. HPLC (254 nm): 95%.

Example 14

Synthesis of Neopentyl 3-hydroxycyclopent-1-ene-1-carboxylate (13)

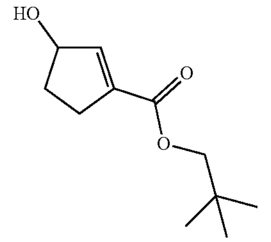

Step 1: To a solution of 3-oxocyclopent-1-ene-1-carboxylic acid 4 (126 mg, 1.0 mmol), 4-dimethylaminopyridine (24 mg, 0.2 mmol) and 2,2-dimethylpropan-1-ol (124 mg, 1.4 mmol) in DCM (9 mL) at 0° C. was added N-(3-dimethylaminopropyl)-N'-ethylcarbodiimide hydrochloride (260 mg, 1.4 mmol) dissolved in DCM (4 mL). The mixture was then allowed to warm to room temperature and stirred for overnight. A solution of saturated $NH_4Cl$ was added to the mixture, which then, was washed with DCM. The combined organic phase was dried over $Na_2SO_4$, filtered, and evaporated in vacuo. Rough purification by column chromatography (Heptane/EtOAc 4:1) furnished impure neopentyl 3-oxocyclopent-1-ene-1-carboxylate (75 mg, 43%) as a yellow oil.

Step 2: Performed as described in example 1 (step 2) using $CeCl_3$, $7H_2O$ (309 mg, 0.8 mmol), neopentyl 3-oxocyclopent-1-ene-1-carboxylate (131 mg, 0.7 mmol), MeOH (7 mL) and $NaBH_4$ (127 mg, 3.4 mmol). Purification by column chromatography (heptane/EtOAc 3:1) furnished neopentyl 3-hydroxycyclopent-1-ene-1-carboxylate (57 mg, 43%) as a transparent oil. $^1H$ NMR (600 MHz, Chloroform-d) δ: 6.71 (q, J=2.1 Hz, 1H), 5.01-4.97 (m, 1H), 3.85 (s, 2H), 2.79-2.73 (m, 1H), 2.54-2.49 (m, 1H), 2.45-2.39 (m, 1H), 1.83-1.78 (m, 1H), 0.97 (s, 9H). $^{13}C$ NMR (151 MHz, Chloroform-d) δ: 165.3, 142.7, 139.4, 77.4, 74.0, 33.8, 31.6, 30.1, 26.6. HPLC (254 nm): 99%.

Example 15

Synthesis of tert-Butyl 3-hydroxycyclopent-1-ene-1-carboxylate (14) (Aye et al, 2008)

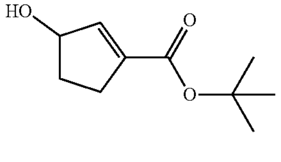

Step 1: To a solution of 3-oxocyclopent-1-ene-1-carboxylic acid 4 (209 mg, 1.7 mmol) in DMF (5 mL), tert-butyl 2,2,2-trichloroacetimidate (3.0 mL, 16.7 mmol) and boron trifluoride diethyl etherate (0.1 mL, 0.9 mmol) were added. The mixture was stirred overnight at 50° C. A solution of saturated $NaHCO_3$ was added and then aqueous phase was extracted with EtOAc. The combined organic phase was dried over anhydrous $Na_2SO_4$, filtered, and evaporated in vacuo to dryness. Rough purification by column chromatography (Heptane/EtOAc 3:1) furnished tert-butyl 3-oxocyclopent-1-ene-1-carboxylate (138 mg, 46%) as a yellow oil.

Step 2: Performed as described in example 1 (step 2) using $CeCl_3$, $7H_2O$ (499 mg, 1.3 mmol), tert-butyl 3-oxocyclopent-1-ene-1-carboxylate (203 mg, 1.1 mmol), MeOH (11 mL) and $NaBH_4$ (213 mg, 5.6 mmol). Purification by column chromatography (heptane/EtOAc 2:1) furnished tert-butyl 3-hydroxycyclopent-1-ene-1-carboxylate (Aye et al, 2008) (25 mg, 12%) as an off-white oil.

Example 16

Synthesis of Lithium(I) (2S)-2-amino-3-(3-(3-hydroxycyclopent-1-ene-1-carboxamido)phenyl)propanoate (15)

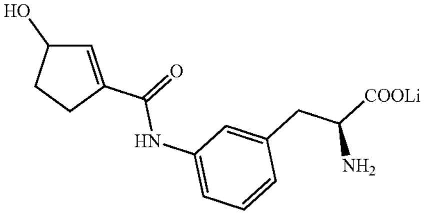

Step 1: 3-Hydroxycyclopent-1-ene-1-carboxylic acid (HOCPCA) (Vogensen et al., 2013) (355 mg, 2.8 mmol), 4-dimethylaminopyridine (35 mg, 0.3 mmol) were dissolved in THF (15 mL), and cooled to 0° C. under argon. Acetic anhydride (0.4 mL, 4.2 mmol) was added dropwise, and stirred overnight at room temperature. Water was added and the mixture was extracted with EtOAc. The combined organic phase was dried over $Na_2SO_4$, filtered, and evaporated in vacuo. Purification by column chromatography (heptane/EtOAc 1:3+1% of AcOH) furnished 3-acetoxycyclopent-1-ene-1-carboxylic acid (434 mg, 92%) as a white solid.

Step 2: 3-Acetoxycyclopent-1-ene-1-carboxylic acid (137 mg, 0.8 mmol), N-(3-dimethylaminopropyl)-N'-ethylcarbodiimide hydrochloride (152 mg, 0.8 mmol), hydroxybenzotriazole (108 mg, 0.8 mmol), triethylamine (0.22 mL, 1.6 mmol) were dissolved in THF (3 mL) and stirred for 10 minutes under argon. Methyl (S)-3-(3-aminophenyl)-2-((tertbutoxycarbonyl)amino)propanoate (281 mg, 1.0 mmol) in THF (3 mL) was added, and the mixture was stirred overnight at room temperature. A solution of saturated $NH_4Cl$ was added to the mixture, which then, was washed with EtOAc. The combined organic phase was dried over $Na_2SO_4$, filtered, and evaporated in vacuo. Purification by column chromatography (Heptane/EtOAc 1:1) afforded methyl (2S)-3-(3-(3-acetoxycyclopent-1-ene-1-carboxamido)phenyl)-2-((tert-butoxycarbonyl)-amino)propanoate (320 mg, 90%) as a yellow solid Step 3: To a solution of methyl (2S)-3-(3-(3-acetoxycyclopent-1-ene-1-carboxamido)phenyl)-2-((tert-butoxycarbonyl)amino)propanoate (139 mg, 0.3 mmol) in dioxane (1.2 mL) was added dropwise with 4M HCl/dioxane (1.2 mL, 4.7 mmol) at 0° C. The mixture was allowed to stir for 1 h at room temperature. A solution of saturated $NaHCO_3$ was added and then aqueous phase was extracted with EtOAc. The combined organic phase was dried over anhydrous $Na_2SO_4$, filtered, and evaporated in vacuo to dryness. Rough purification by column chromatography (EtOAc/MeOH 5:1) furnished corresponding intermediate as a yellow oil. LiOH (4 mg, 0.2 mmol) in water (0.5 mL) was added to a solution of intermediate in MeOH (0.5 mL). The mixture was stirred at room temperature until full conversion. The mixture was evaporated in vacuo to dryness to afford lithium(I) (2S)-2-amino-3-(3-(3-hydroxycyclopent-1-ene-1-carboxamido)phenyl)propanoate (30 mg, 34%) as an off-white solid. $^1H$ NMR (400 MHz, Methanol-$d_4$) δ: 7.62 (ddd, J=8.1, 2.2, 1.0 Hz, 1H), 7.33 (t, J=1.9 Hz, 1H), 7.25 (t, J=7.9 Hz, 1H), 7.05 (dt, J=7.6, 1.4 Hz, 1H), 6.61 (q, J=2.1 Hz, 1H), 4.94 (tdd, J=5.2, 2.6, 1.6 Hz, 1H), 3.47 (dd, J=8.1, 4.7 Hz, 1H), 3.10 (dd, J=13.5, 4.7 Hz, 1H), 2.86-2.73 (m, 2H), 2.65-2.50 (m, 1H), 2.43-2.35 (m, 1H), 1.85-1.76 (m, 1H). $^{13}C$ NMR (151 MHz, Methanol-$d_4$) δ: 181.4, 166.3, 143.0, 140.9, 139.9, 139.4, 129.8, 126.8, 123.1, 120.4, 77.9, 58.9, 42.7, 34.1, 31.1. HPLC (254 nm): 99%.

Example 17

GHB-Related Analogues Bind with High Affinity to Specific GHB Sites in Rat Brain Synaptic Membranes at Both pH Values of 6.0 and 7.4 (FIG. 1)

Novel analogues were tested in established binding assays and compared to reference compounds. At pH 6, compounds 1-10 were found to inhibit A)$^3$H-B binding (respective $K_i$ values of 50, 92, 30, 52, 53, 108, 325, 225, 382, 9687 nM) compared to compound B with a $K_i$ value of 440 nM. B) Compounds 1, 2 and 3 also inhibited $^3$H-A binding in a concentration-dependent manner with similar affinities (respective $K_i$ values of 56 nM, 144 nM and 50 nM) compared to GHB itself with a $K_i$ value of 2.75 μM. C) At pH 7.4, lower affinities were obtained in the $^3$H-A binding assay, yielding $K_i$ values for compounds 1, 2 and 3 of ~267, 604 and 87 nM, respectively. The known CAMK2A inhibitor CN21 failed to displace $^3$H-A binding at concentrations up to 30 μM (~300-fold its reported $IC_{50}$ value). D) Competition of compounds C, diclofenac and 4'-hydroxydiclofenac in the $^3$H-A binding assay showed superior affinity of compound C relative to 4'-hydroxydiclofenac and diclofenac ($K_i$ values of 22 nM vs. 16 μM and 4.7 μM).

Example 18

Lack of Noticeable $GABA_B$ Receptor Binding of GHB Analogues (FIG. 2)

GHB, compounds A and C were tested for affinity for the $GABA_B$ receptor in an established binding assay. Whereas GHB at both 0.1 mM and 1 mM could inhibit $^3$H-$GABA_B$ binding, compound A displayed no ability to compete up to concentrations of 1 mM and compound C showed limited inhibition at a concentration of 1 mM.

Example 19

Compound a does not Produce Hypothermia in Mice, but GBL does (FIG. 3)

To confirm the inability of compound A to functionally activate the $GABA_B$ receptor, the known $GABA_B$ effect of hypothermia was studied in mice by comparing administration of the GHB prodrug GBL (750 mg/kg) and compound A (500 mg/kg) in wild-type and $GABA_B$ receptor knock-out mice (Kaupmann et al., 2003). As expected, GBL was able to promote a strong decreased in body temperature. By contrast, compound A had no effect on hypothermia in either wild-type or knock-out mice.

Example 20

GBL Induces a Reduction in the Cerebral Metabolic Rate of Glucose not Mediated by $GABA_B$ Receptors (FIG. 4)

To confirm that the GHB prodrug GBL alters glucose metabolism via a non-$GABA_B$ receptor-dependent mechanism, either saline (black bars) or GBL (200 mg/kg) (white bars) were administered (i.p.) to $GABA_{B1}$ receptor knock-out mice. Ten min later, $^{14}$C-deoxyglucose was administered (i.p.) to all mice to estimate brain glucose consumption. This showed a significant GHB-induced lowering of the cerebral metabolic rate of glucose in frontal cortex and hippocampus after 45 min (10.46 vs. 6.78 nCi/ROI/min for frontal cortex and 9.74 vs. 6.45 for hippocampus, *P<0.05, error bars depicted as SD).

Example 21

Compound A Reduces Infarct Size when Administered 30 Min after Photothrombotic Focal Ischemia (FIG. 5)

A) Compound A in two different doses was administered to mice 30 min after induction of a focal stroke to the cerebral cortex and compared to saline-treated animals. Three days after the induced stroke, an infarct was visible in the left motor cortex. B) Quantification of infarct volumes revealed a 30% reduction when comparing saline with compound A (175 mg/kg) (9.38 vs. 6.56 $mm^3$, ***P<0.0005). The group of mice receiving the low dose (17.5 mg/kg) did not show a significant reduction in infarct volume compared to saline (9.38 vs. 8.95 $mm^3$).

Example 22

Compound A Improves Motor Performance in Affected Limbs when Administered 30 Min after Photothrombotic Focal Ischemia (FIG. 6)

To evaluate improvement of motor function following administration of compound A after focal ischemia, the cylinder task and the grid-walking task were used as specific measures for left forelimb motor recovery. Asymmetry was observed between left and right forelimb in the cylinder and grid-walking tasks 3 days after focal ischemia. A) In the grid-walking task, the group of mice that received the high dose (175 mg/kg), demonstrated an improvement of 26% compared to the saline-treated group (**P<0.01), while a non-significant reduction (10%) was observed for the 17.5 mg/kg group. B) The asymmetry measured with the cylinder task was significantly reduced when administering compound A for both the 17.5 and the 175 mg/kg dose groups with effects of 40% and 42%, respectively.

Example 23

Compound a Reduces Infarct Size when Administered 3, 6 or 12 Hrs after Photothrombotic Focal Ischemia (FIG. 7)

To evaluate later treatment efficacy, compound A was given 3, 6 or 12 hrs after induction of the infarct at two different doses. A) Administration of compound A (175 mg/kg) 3, 6 or 12 hrs after the stroke significantly decreased infarct sizes (5.51 $mm^3$ vs. 3.12, 3.68 and 3.58 $mm^3$, respectively) (P<0.01-0.05), amounting to a 33-43% decrease. For comparison, GHB (275 mg/kg) at the 3 hr time point did not result in a significant decrease in infarct size (not shown) B) Administration of a lower dose of compound A (90 mg/kg) 3 hrs after the stroke significantly decreased infarct size by 51% (5.55 $mm^3$ vs. 2.68 $mm^3$, **P<0.01).

Example 24

Compound A Improves Motor Performance in Affected Limbs when Administered 3, 6 or 12 Hrs after Photothrombotic Focal Ischemia (FIG. 8)

To assess motor skills in the treatment group receiving a 175 mg/kg dose of A at the later time points of administration after the induction of the infarct, asymmetry was measured between left and right forelimb in the grid-walking and cylinder tasks 7 days after the focal ischemia. A) The asymmetry measured with the grid-walking task was highly significantly reduced for both 3, 6 and 12 hr treatment points (effects of 31, 22 and 21%, respectively (***P<0.001). B) In the cylinder task an improvement of 16% and 20% compared to the saline-treated group was observed for the 3 hr (*P<0.05) and 6 hr (**P<0.001) time points, respectively, whereas the 12 hr point was non-significant.

Example 25

Compound 2 Reduces Infarct Size and Improves Motor Performance in Affected Limbs when Administered 3 or 6 Hrs after Photothrombotic Focal Ischemia (FIG. 9)

The novel compound 2 was given (i.p.) 3 or 6 hrs after induction of the infarct at doses of 175 mg/kg (A-C) or 50 mg/kg (D-F). A) Administration of 2 (175 mg/kg), 3 or 6 hrs after the injury significantly decreased infarct sizes (5.55 $mm^3$ vs. 3.44 and 2.98 $mm^3$, respectively, P<0.01-0.05), amounting to a 38-46% decrease. Compound 2 administration significantly reduced B) number of foot faults (*P<0.05) for the 6 hr group, and C) time spent on affected paw for both 3 and 6 hrs (P<0.01-0.001) compared to the saline-treated mice. D) Administration of 2 (50 mg/kg) promoted similar protection 3 hrs after the injury significantly decreased infarct size by 39% (5.55 $mm^3$ vs. 3.4 $mm^3$, **P<0.01). Similarly, mice treated with the lower dose displayed E-F) significantly improved motor performance in both asymmetry tests.

Example 26

Compound A Treatment Reduces the Expression of Selected Molecular Markers Related to Photothrombotic Focal Ischemia (FIG. 10)

To investigate the protective mechanisms against brain damage following a focal ischemic insult, mRNA expression levels of the markers GFAP, CD14 and MMP9 were measured in the brain tissue surrounding the ischemic core 3 days post-stroke. A) GFAP levels were markedly increased in the stroked animals, but the levels were not different between the two treatment groups. B) C) By contrast, the mRNA levels of CD14 and MMP9 were markedly lowered in animals that received compound A (175 mg/kg) 30 min following the focal ischemic event. Already at the low dose of A (17.5 mg/kg), MMP9 mRNA levels were significantly lower than in animals receiving saline. D) Similar results were found after 12 hrs.

Example 27

Compound A Treatment Reduces Plasma Levels of Selected Pro-Inflammatory Cytokines in Photothrombotic Focal Ischemia (FIG. 11)

To evaluate the inflammatory response at early time points, blood samples were collected 4 hrs after induction of a focal ischemic event. A) The formation of the infarct significantly increased the levels of MCP-1, IL-6 and IL-1a. MCP-1 levels showed a tendency towards a decrease in plasma in the compound A-treated animals after 4 hrs. B) Treatment with compound A significantly lowered the plasma levels of IL-6 compared to saline-treated mice. C) Treatment with A did not significantly affect IL-1a levels compared to saline-treated mice.

Example 28

Compound A Reduces Infarct Size in the Permanent Middle Cerebral Artery Occlusion (pMCAO) Model of Focal Ischemia (FIG. 12)

Compound A (175 mg/kg) was administered to mice 30 min after induction of a focal stroke via a permanent occlusion of the middle cerebral artery and compared to saline-treated animals. Three days after the induced stroke, an infarct was visible in the left motor cortex. Quantification of infarcts revealed a significant reduction in infarct volume when comparing saline with A (175 mg/kg) after 30 min (16.6 vs. 12.3 $mm^3$, *P<0.05).

Example 29

Compound A Improves Functional Recovery when Administered 30 Min after a pMCAO Focal Lesion (FIG. 13)

Compound A (175 mg/kg) was administered to mice 30 min after induction of a focal stroke via a permanent occlusion of the middle cerebral artery and compared to saline-treated animals and both motor- and sensory impairment was investigated using rotarod, grip strength and Hargreaves tests.

In the rotarod test, the mice were exposed to 4 trials (T1-T4) 48 hrs post-stroke. A) Saline-treated mice in the rotarod learned significantly from T2 to T3). B) In comparison, the mice receiving treatment with A had a steeper learning curve (T1 to T2), although time spent on the rotarod in T4 did not differ between groups. C) Three days following stroke, saline-treated mice demonstrated a significant deficit in grip strength in the affected fore limb, while the Compound A-treated mice did not demonstrate any deficit in this test. D) Similarly, for the evaluation of sensory deficits in the affected fore limb, the saline-treated mice showed an increased response time in the Hargreaves test for the affected forelimb, while this was not evident for the mice treated with A.

Example 30

Ex Vivo $^3$H-A Radioligand Binding in Coronal Brain Sections from Mouse Brain (FIG. 14)

$^3$H-A was used to perform ex vivo binding to C57BL/6J mice. Thus, in a design with 5 mice per group, $^3$H-A (5 MBq per mouse) was injected i.p. After 30 min, the brains were dissected and autoradiography performed. Significant specific binding levels were observed in the hippocampus and cortex compared to the cerebellum, used for normalization.

Example 31

Identification of CAMK2A as the GHB High-Affinity Binding Site (FIG. 15)

A) Principle of photoaffinity labelling workflow. Crude synaptic membranes from rat hippocampus were incubated with the photoaffinity ligand SBV3 and UV-irradiated (wavelength 302 nm) to covalently link the photoaffinity ligand to the GHB binding protein. After introduction of biotin through a Staudinger-Bertozzi ligation to EZ-Link™ Phosphine-PEG$_3$-Biotin (ThermoFisher Scientific), the biotin-labelled proteins were affinity-purified and subjected to LC-MS/MS analysis. B) The anti-biotin western blot shows the specifically labelled band at ~55 kDa in the presence (first lane) and absence (second lane) of photoligand. C)$^3$H-A binding to cortical membranes from CAMK2A and CAMK2B knock-out mouse brains. D)$^3$H-A binding to whole cell homogenate from HEK293T cells transfected with rat CAMK2A displayed significantly higher total binding compared to non-specific levels (87% specific binding) whereas no specific binding was seen at CAMK2B (black bars=specific binding, white bars=non-specific binding; 1 mM GHB).

Example 32

GHB and the GHB-Related Analogues A, B, C, 1 and 2 Bind Directly to Recombinant CAMK2A (FIG. 16)

Human/rat CAMK2A expressed in HEK cells was assayed in an in-house established $^3$H-A filtration binding assay performed on whole cell lysates of CAMK2A-transfected HEK293T cells. As seen for binding to synaptic membranes from rat brain cortex, compounds GHB, A, B, C, 1 and 2 were able to concentration-dependently inhibit radioligand binding. Obtained K values were 50.4, 1.95, 3.71, 0.81, 0.72 and 1.09 μM, respectively, compounds 1 and 2 displaying up 50-70 times better affinity than GHB in competition with the $^3$H-A radioligand, which is similar to the binding potency shift observed in the $^3$H-A binding assay (FIG. 1B).

Example 33

Compounds A and 2 Rapidly Cross tsA201 Cell Membranes Through their Substrate Activity at Proton-Coupled Transporters (FIG. 17)

To monitor the ability of compounds to enter into cells and reach the target (CAMK2A), a fluorescence-based assay with the pH-sensitive dye BCECF was employed. Cells (tsA201; related to HEK293-T) known to express MCTs were grown in 96-well plates and exposed to compounds and pH-decreased measured for 2 min. A) As expected for A, a known MCT1 substrate, a concentration-dependent decrease in pH was observed ($EC_{50}$ value of 8.2 mM). B) Compound 2, representative of several of the analogues, similarly produced a concentration-dependent decrease in pH ($EC_{50}$ value of 1.6 mM), supporting compound delivery into the cell cytosol.

Example 34

Compound a Prevents pThr286 CAMK2A Autophosphorylation in Mice Subjected to Photothrombotic Focal Ischemia (FIG. 18)

To assess functional activity of A, the well-described pThr286 assay (Kool et al., 2016) was used on cortical tissue isolated from mice subjected to photothrombotic injury with and without treatment with A.

To this end, sham mice or mice were treated with either saline or 175 mg/kg A (i.p.) 3 hrs after the injury. Thirty (30) min after the injury, mice were sacrificed and cortex tissue processed. Autophosphorylation was assessed by Western blot analysis and levels of pThr286 CAMK2A normalized to total CAMK2A to detect changes in autophosphorylation. In accordance with other reports on ischemia (Ahmed et al., 2017), focal ischemia induced by photothrombosis significantly increased autophosphorylation (#P<0.05). This response was significantly inhibited by compound A (*P<0.05) amounting to a 73% decrease in autophosphorylation compared to the sham condition.

REFERENCES

Ahmed, M. E., Dong, Y., Lu, Y., Tucker, D., Wang, R., Zhang, Q., 2017. Beneficial effects of a CaMKIIa inhibitor TatCN21 peptide in global cerebral ischemia. J Mol Neurosci 61, 42-51.

Aye, Y.; Davies, S. G., Garnaer, A. C., Roberts, P. M., Smith, A. D.; Thomson, J. E., 2008 Parallel kinetic resolution of citertci-butyl (RS)-3-oxy-substituted cyclopent-1-ene-carboxylates for the asymmetric synthesis of 3-oxy-substituted cispentacin and transpentacin derivaties. Organic Biomol Chem 6, 2195-2203.

Clarkson, A. N., Huang, B. S., Macisaac, S. E., Mody, I., Carmichael, S. T., 2010. Reducing excessive GABA-mediated tonic inhibition promotes functional recovery after stroke. Nature 468, 305-309.

Coultrap, S. J., Ashpole, N. M., Hudmon, A., Bayer, K. U., 2011. CaMKII in cerebral ischemia. Acta Pharmacol Sin 32, 861-872.

Gruber, R; Cagniant, D., Cagniant, P., 1983. Hydrocarbures arylaliphatiques. Partie VII. Orientation dans la reaction de bromation de benzocyclenes bi-et tricycliques superieurs. Bulletin de la Societe Chimique de France, 2, 96-104.

Kaupmann, K., Cryan, J. F., Wellendorph, P., Mombereau, C., Sansig, G., Klebs, K., Schmutz, M., Froestl, W., van der Putten, H., Mosbacher, J., Brauner-Osborne, H., Waldmeier, P., Bettler, B., 2003. Specific γ-hydroxybutyrate-binding sites but loss of pharmacological effects of γ-hydroxybutyrate in $GABA_{B1}$-deficient mice. Eur J Neurosci 18, 2722-2730.

Klein, A. B., Bay, T., Villumsen, I. S., Falk-Petersen, C. B., Marek, A., Frølund, B., Clausen, R. P., Hansen, H. D., Knudsen, G. M., Wellendorph, P., 2016. Autoradiographic imaging and quantification of the high-affinity GHB binding sites in rodent brain using $^3$H-HOCPCA. Neurochem Int 100, 138-145.

Kool, M. J., Van De Bree, J. E., Bodde, H. E., Elgersma, Y., Van Woerden, G. M., 2016. The molecular, temporal and region-specific requirements of the beta isoform of Calcium/Calmodulin-dependent protein kinase type 2 (CAMK2B) in mouse locomotion. Sci Rep 6:26989, 1-12.

Kuschinsky, W., Suda, S., Sokoloff, L., 1985. Influence of gamma-hydroxybutyrate on the relationship between local cerebral glucose utilization and local cerebral blood flow in the rat brain. J Cereb Blood Flow Metab 5, 58-64.

Lie, M. E. K., Johansen, N. B., Gowing E. K., Dalby, N. O., Thiesen, L., Wellendorph, P., Clarkson, A. N., In Press. The GAT3 selective substrate L-isoserine upregulates GAT3 expression and increases functional recovery after a focal ischemic stroke in mice. J Cereb Blood Flow Metab doi: 10.1177/0271678X17744123.

Murineddu, G., Ruiu, S., Loriga, G., Manca, I., Lazzari, P., Reali, R., Pani, L.; Toma, L., Pinna, G. A., 2005. Tricyclic pyrazoles. 3. Synthesis, biological evaluation, and molecular modeling of analogues of the cannabinoid antagonist 8-chloro-1-(2',4'-dichlorophenyl)-N-piperidin-1-yl-1,4,5,6-tetrahydrobenzo[6,7]cyclohepta[1,2-c]pyrazole-3-carboxamide. J Med Chem 48, 7351-7362.

Thiesen, L., Kehler, J., Clausen, R. P., Frolund, B., Bundgaard, C., Wellendorph, P., 2015. In vitro and in vivo evidence for active brain uptake of the GHB analog HOCPCA by the monocarboxylate transporter subtype 1. J Pharmacol Exp Ther 354, 166-174.

Vest, R. S., Davies, K. D., O'Leary, H., Port, J. D., Bayer, K. U., 2007. Dual mechanism of a natural CaMKII inhibitor. Mol Cell Biol 18, 5024-5033.

Vogensen, S. B., Marek, A., Bay, T., Wellendorph, P., Kehler, J., Bundgaard, C., Frolund, B., Pedersen, M. H., Clausen, R. P., 2013. New synthesis and tritium labeling of a selective ligand for studying high-affinity γ-hydroxybutyrate (GHB) binding sites. J Med Chem. 56, 8201-8205.

Waxham, M. N., Grotta, J. C., Silva, A. J., Strong, R., Aronowski, J., 1996. Ischemia-induced neuronal damage: a role for calcium/calmodulin-dependent protein kinase II. J Cereb Blood Flow Metab 16, 1-6.

Wellendorph, P., Hog, S., Greenwood, J. R., de Lichtenberg, A., Nielsen, B., Frolund, B., Brehm, L., Clausen, R. P., Bräuner-Osborne, H., 2005. Novel cyclic γ-hydroxybutyrate (GHB) analogs with high affinity and stereoselectivity of binding to GHB sites in rat brain. J Pharmacol Exp Ther 315, 346-351.

Items

1. A compound according to formula I (formula I)

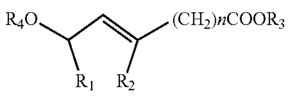

wherein $R_1$ and $R_2$ form a ring system to obtain a compound selected from (formula II)

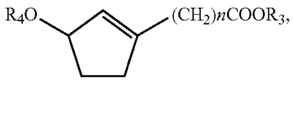

-continued (formula III)

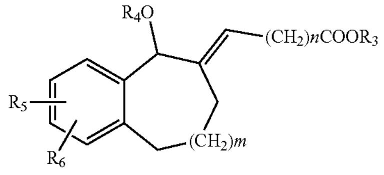

or (formula IV)

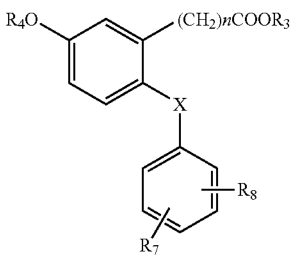

wherein n is 0 or 1;

$R_3$ is selected from H, -Me, -Et, —Pr, -iPr, -Bu, -tBu, -benzyl, polyethylenglycolyl (PEG), or a group such as

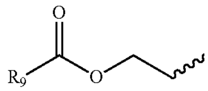

or

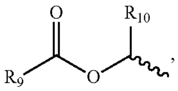

, wherein $R_9$ is selected from -Me, -Et, —Pr, -iPr, -Bu, -iBu, or -tBu, and wherein $R_{10}$ is selected from H, -Me, -Et, -iPr;

$R_4$ is selected from H, —C(═O)-Me, —C(═O)-Et, —C(═O)—Pr, —C(═O)-iPr, —C(═O)—Bu, —C(═O)-tBu, —C(═O)-benzyl, polyethylenglycolyl (PEG), or a groups such as

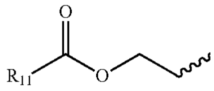

or

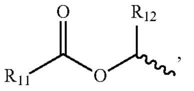

, wherein $R_{11}$ is selected from -Me, -Et, —Pr, -iPr, -Bu, iBu, or -tBu, and wherein $R_{12}$ is selected from H, -Me, -Et, -iPr;

$R_5$, $R_6$, $R_7$, and $R_8$ are independently from each other selected from H, F, Cl, Br, I, aryl, straight or branched $C_{1-8}$ alkyl, —$CH_2(CH_2)_p$-aryl, —CH═CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1;

m is 0 or 1; and

X is N, O, S, $CH_2$ or a pharmaceutically acceptable salt thereof;

with the proviso that the compound is not one of the following:

(A)

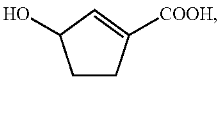

-continued (B)

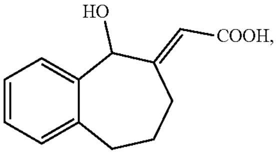

(C)

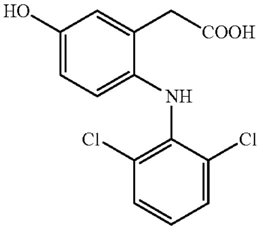

2. A compound according to item 1 having formula II or III, and wherein n is 0.
3. A compound according to item 1 having formula IV, and wherein n is 1
4. A compound according to any of the preceding items, wherein one of $R_3$ and $R_4$ is H.
5. A compound according to any of the preceding item, wherein both $R_3$ and $R_4$ are H.
6. A compound according to any of the preceding items having formula III, wherein $R_5$ is H and $R_6$ is in the 2 position.
7. A compound according to any of the preceding items having formula III, wherein $R_5$ is H and $R_6$ is selected from H, F, Cl, Br, I, aryl, straight or branched $C_{1-8}$ alkyl, $—CH_2(CH_2)_p$-aryl, or —CH═CH-aryl.
8. A compound according to any of the preceding items having formula III, wherein $R_5$ is H and $R_6$ is selected from H, F, Cl, Br, I, Ph, or —CH═CH-aryl.
9. A compound according to any of the preceding items having formula III, wherein $R_5$ is H and $R_6$ is selected from H, F, Cl, Br, I, Ph, or —CH═CH-phenyl.
10. A compound according to any of items 1-4, 5-9, wherein $R_3$ is selected from

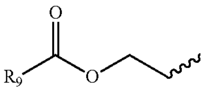 or 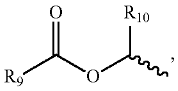, or $R_4$ is selected from

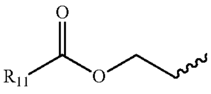 or 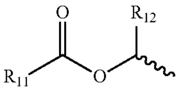

11. A compound according to items 1-4, 5-10, wherein $R_3$ is

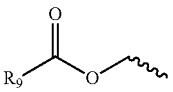

12. A compound according to any of items 1-4, 10 having formula II, wherein $R_4$ is H and $R_3$ is

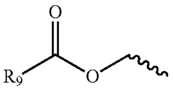

13. A compound according to any of the preceding items having one of the following structures (1)

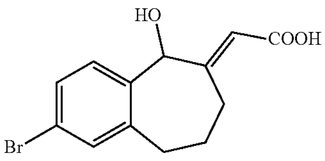

(2)

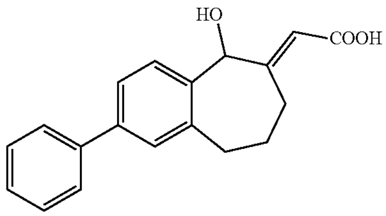

(3)

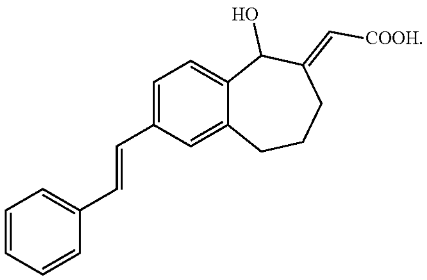

14. A compound according to any of the preceding items for use in medicine.
15. A compound according to any of the preceding items for use in the treatment of acute brain injury as defined herein.
16. Use of a compound according to any of claim 1-13 for the manufacture of a medicament for the treatment of acute brain injury as defined herein.
17. A method for treating a subject suffering from acute brain injury, the treatment comprises administering to said subject an effective amount of a compound as defined in any of items 1-13.
18. A compound according to formula I (formula II)

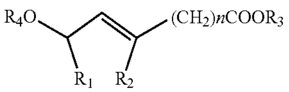

wherein $R_1$ and $R_2$ form a ring system to obtain a compound selected from (formula II)

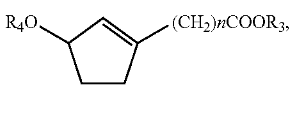

-continued (formula III)

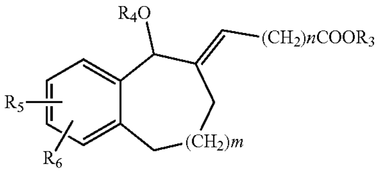

or (formula IV)

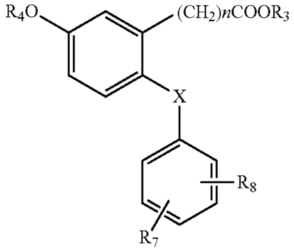

wherein n is 0 or 1;

$R_3$ is selected from H, -Me, -Et, —Pr, -iPr, -Bu, -tBu, -benzyl, polyethylenglycolyl (PEG), or a group such as

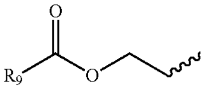

or

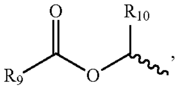

, wherein $R_9$ is selected from -Me, -Et, —Pr, -iPr, -Bu or -tBu, and wherein $R_{10}$ is selected from H, -Me, -Et, -iPr;

$R_4$ is selected from H, —C(=O)-Me, —C(=O)-Et, —C(=O)—Pr, —C(=O)-iPr, —C(=O)—Bu, —C(=O)-tBu, —C(=O)-benzyl, polyethylenglycolyl (PEG), or a groups such as

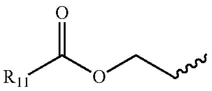

or

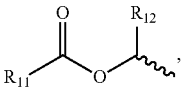

, wherein $R_{11}$ is selected from -Me, -Et, —Pr, -iPr, -Bu or -tBu, and wherein $R_{12}$ is selected from H, -Me, -Et, -iPr;

$R_5$, $R_6$, $R_7$, and $R_8$ are independently from each other selected from H, F, Cl, Br, I, aryl, straight or branched $C_{1-8}$ alkyl, —$CH_2(CH_2)_p$-aryl, —CH=CH-aryl, $NH_2$, $NO_2$, OH, SH, straight or branched —O—$C_{1-8}$ alkyl, straight or branched —S—$C_{1-8}$ alkyl, straight or branched —NH—$C_{1-8}$ alkyl, —O-aryl, —S-aryl, —NH-aryl, wherein aryl includes aryl having one or more heteroatoms selected from O, N or S, and wherein p is 0 or 1;

m is 0 or 1; and

X is N, O, S, $CH_2$ or a pharmaceutically acceptable salt thereof for use in the treatment of acute brain injury.

19. A compound for use according to item 18, wherein the compound is selected from (A)

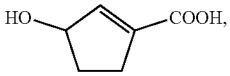

, (B)

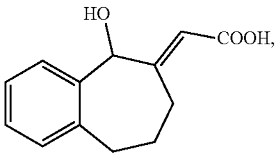

, (C)

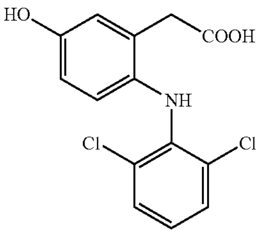

The invention claimed is:

1. A compound according to formula I formula I

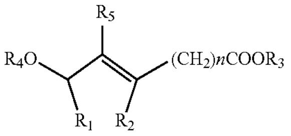

or a pharmaceutically acceptance salt thereof, wherein:

i) $R_5$ is H, $R_1$ and $R_2$ form a ring system, and said compound is selected from:

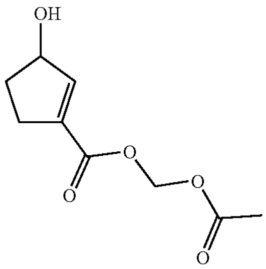

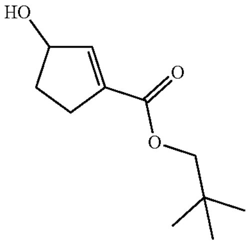

or a compound of formula IV:

formula IV

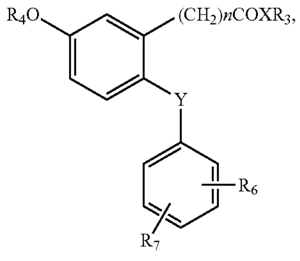

wherein:

n is 1;

X is selected from O and NH

Y is selected from NH, O, and $CH_2$ $R_3$ is selected from H, linear or branched $C_1$-$C_6$ alkyl, benzyl, polyethylenglycolyl,

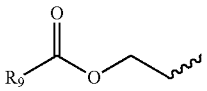

and

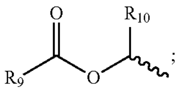

;

$R_9$ is selected from linear and branched $C_1$-$C_6$ alkyl;

$R_{10}$ is selected from H, -Me, -Et, —Pr, -iPr, -Bu, -iBu, -tBu, pentyl, neopentyl, and hexyl;

$R_4$ is selected from H, —C(═O)—$C_1$-$C_6$-alkyl; —C(═O)-benzyl, polyethylenglycolyl,

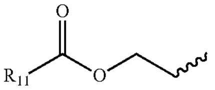 and 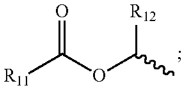 ;

$R_{11}$ is selected from linear and branched $C_1$-$C_6$ alkyl;

each instance of is a bond;

$R_{12}$ is selected from H, -Me, -Et, —Pr, -iPr, -Bu, -iBu, -tBu, pentyl, neopentyl, and hexyl;

$R_6$ and $R_7$ are each independently selected from H, F, Cl, Br, I, aryl, straight linear or branched $C_{1-8}$ alkyl, —$CH_2(CH_2)_p$-aryl, —CH═CH-aryl, $NH_2$, $NO_2$, OH, SH, linear or branched —O—$C_{1-8}$ alkyl, linear or branched —S—$C_{1-8}$ alkyl, linear or branched —NH—$C_{1-8}$ alkyl, —O-aryl, —S-aryl, and —NH-aryl;

wherein aryl optionally includes one or more heteroatoms selected from O, N and S; and wherein p is 0 or 1; or ii) $R_2$ is H, $R_1$ and $R_5$ form a ring system, and said compound is a compound of formula IIIb, formula IIIc, or formula IIId:

formula IIIb

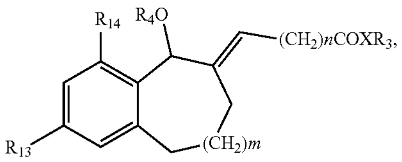

formula IIIc

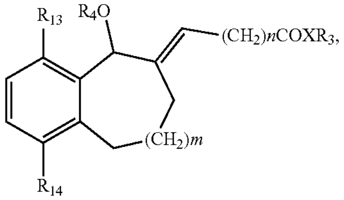

formula IIId

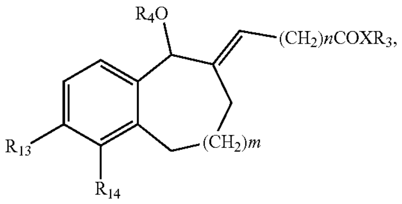

wherein:

n is 0 or 1;

X is selected from O and NH;

m is 0 or 1;

$R_3$ is selected from H, linear or branched $C_1$-$C_6$-alkyl; -benzyl, polyethylenglycolyl,

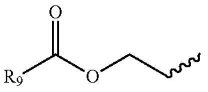 and 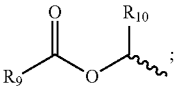 ;

$R_9$ is selected from linear and branched $C_1$-$C_6$ alkyl;

$R_{10}$ is selected from H, -Me, -Et, —Pr, -iPr, -Bu, -iBu, -tBu, pentyl, neopentyl, and hexyl;

$R_4$ is selected from H, —C(═O)—$C_1$-$C_6$-alkyl; —C(═O)-benzyl, polyethylenglycolyl,

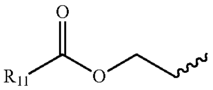 and 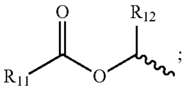 ;

each instance of is a bond;

$R_1$ is selected from linear and branched $C_1$-$C_6$ alkyl; $R_{12}$ is selected from H, -Me, -Et, —Pr, -iPr, -Bu, -iBu, -tBu, pentyl, neopentyl, and hexyl;

$R_{13}$, is selected from H, F, Br, aryl, linear or branched $C_{1-8}$ alkyl, —$CH_2(CH_2)_p$-aryl, —CH═CH-aryl, $NH_2$, $NO_2$, OH, SH, linear or branched —O—$C_{2-8}$ alkyl, linear or branched —S—$C_{1-8}$ alkyl, linear or branched —NH—$C_{1-8}$ alkyl, —O-aryl, —S-aryl, and —NH-aryl, $R_{14}$ is selected from H, F, Cl, Br, aryl, linear or branched $C_{1-8}$ alkyl, —$CH_2(CH_2)_p$-aryl, —CH═CH-aryl, $NH_2$, OH, SH, linear or branched —O—$C_{1-8}$ alkyl, linear or branched —S—$C_{1-8}$ alkyl, linear or branched —NH—$C_{1-8}$ alkyl, —O-aryl, —S-aryl, and —NH-aryl, each aryl optionally includes one or more heteroatoms selected from O, N and S, and wherein each instance of p is independently 0 or 1;

with the proviso that the compounds of formula IV, when $R_4$ is H or $H_3$ or $CH_3$, then:

i) $R_6$ and $R_7$ are not both Cl, ii) $R_6$ and $R_7$ are not both methyl, iii) when $R_6$ is Cl then $R_7$ is not F, and iv) when $R_6$ is F then $R_7$ is not Cl . . .

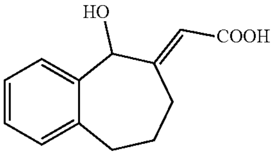

or

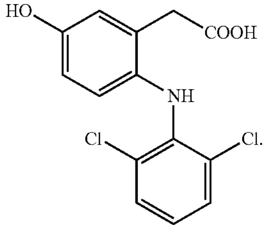

2. The compound according to claim 1, wherein:

said compound is the compound of formula IIIb, the compound of formula IIIc or the compound of formula IIId, and wherein n is 0.

3. The compound according to claim 1, wherein said compound is the compound of formula IV, wherein $R_3$ is selected from H, -Me, -Et, —Pr, -iPr, -Bu, -tBu, -iBu, pentyl, neopentyl, hexyl; -benzyl, polyethylenglycolyl

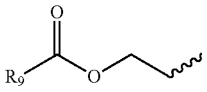 and 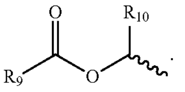 .

4. The compound according to claim 1, wherein said compound is the compound of formula IV, and wherein $R_4$ is selected from H, —C(═O)-Me, —C(═O)-Et, —C(═O)—Pr, —C(═O)-iPr, —C(═O)—Bu, —C(═O)-tBu; —C(═O)-benzyl, polyethylenglycolyl

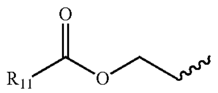 and 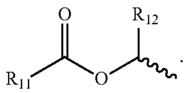.

5. The compound according to claim 1, wherein said compound is the compound of formula IIIb, the compound of formula IIIc, or the compound of formula IIId, and wherein $R_3$ is selected from H, -Me, -Et, —Pr, -iPr, -Bu, -tBu, -iBu, pentyl, isopentyl, hexyl, -benzyl, polyethylenglycolyl,

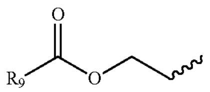 and 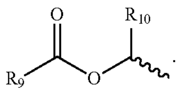.

6. The compound according to claim 1, wherein said compound is the compound of formula IIIb, the compound of formula IIIc, or the compound of formula IIId, and wherein $R_4$ is selected from H, —C(═O)-Me, —C(═O)-Et, —C(═O)—Pr, —C(═O)-iPr, —C(═O)—Bu, —C(═O)-tBu; —C(═O)-benzyl, polyethylenglycolyl, r

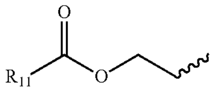 and 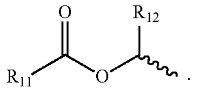.

7. The compound according to claim 1, wherein said compound is the compound of formula IIIb, the compound of formula IIIc, or the compound of formula IIId, wherein:

i) $R_{13}$ is H and $R_{14}$ is selected from H, F, Cl, Br, aryl, linear or branched $C_{1-8}$ alkyl, $—CH_2(CH_2)_p$-aryl, and —CH═CH-aryl, or ii) wherein $R_{14}$ is H and $R_{13}$ is selected from H, F, Br, aryl, linear or branched $C_{1-8}$ alkyl, $—CH_2(CH_2)_p$-aryl, and —CH═CH-aryl.

8. The compound according to claim 1, wherein said compound is the compound of formula IIIb, the compound of formula IIIc, or the compound of formula IIId, wherein:

i) $R_{13}$ is H and $R_{14}$ is selected from H, F, Cl, Br, Ph, and —CH═CH-phenyl, or ii) $R_{14}$ is H and $R_{13}$ is selected from H, F, Br, Ph, and —CH═CH-phenyl.

9. The compound according to claim 1, wherein said compound is the compound of formula IIIb, the compound of formula IIIc, or the compound of formula IIId, wherein:

i) n=0, $R_3$ is H, X is O, $R_4$ is H, $R_{13}$ is selected from H, F, Br, phenyl, and methyl, and $R_{14}$ is H, or ii) n=0, $R_3$ is H, X is O, $R_4$ is H, $R_{14}$ is selected from H, F, Cl, Br, phenyl, and methyl, and $R_{13}$ is H.

10. The compound according to claim 1, wherein said compound is the compound of formula IIIb, the compound of formula IIIc, or the compound of formula IIId, wherein:

i) n=0, $R_3$ is selected from H, -Me, -Et, —Pr, -iPr, -Bu, and -tBu; X is O, $R_4$ is H, $R_{13}$ is selected from H, F, Br, phenyl, and methyl, and $R_{14}$ is H, or ii) n=0, $R_3$ is H, X is O, $R_4$ is H, $R_{14}$ is selected from H, F, Cl, Br, phenyl, and methyl, and $R_{13}$ is H.

11. A method of treating acute brain injury, said method comprising administering a compound according to claim 1 to a subject in need thereof, thereby treating the acute brain injury in the subject.

12. The method according to claim 11, wherein the compound is the compound of formula IIIb, the compound of formula IIIc, or the compound of formula IIId.

13. The method according to claim 11, wherein:

i) said compound is

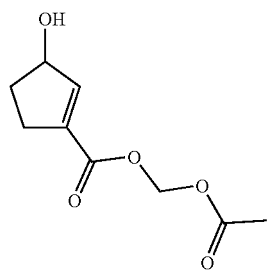 or 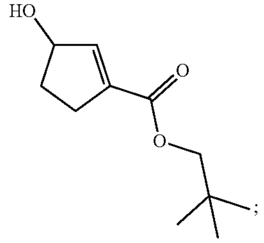;

ii) said compound is the compound of formula IIIb, the compound of formula IIIc, or the compound of formula IIId, and n is 0, or iii) said compound is the compound of formula IV.

14. The method according to claim 11, wherein said compound is selected from

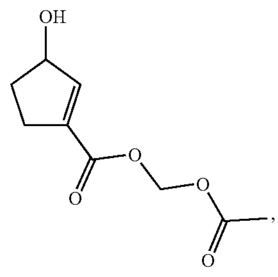, 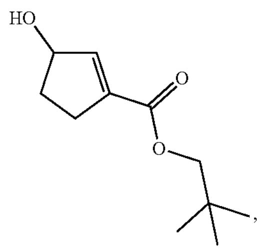, and the compound of formula IV, and wherein $R_3$ is selected from H, -Me, -Et, —Pr, -iPr, -Bu, -tBu, -iBu, pentyl, neopentyl, and hexyl; -benzyl, polyethylenglycolyl,

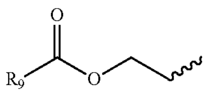 and 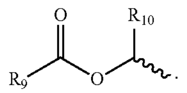.

15. The method according to claim 11, wherein said compound is selected from

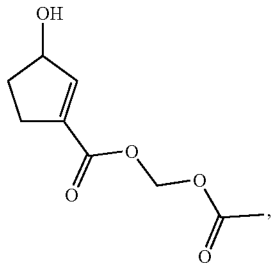

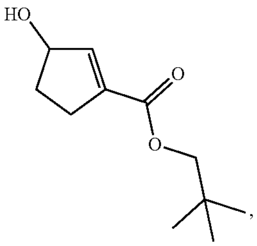

and the compound of formula IV, and wherein $R_4$ is selected from H, —C(═O)-Me, —C(═O)-Et, —C(═O)—Pr, —C(═O)-iPr, —C(═O)—Bu, and —C(═O)-tBu; —C(═O)-benzyl, polyethylenglycolyl,

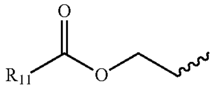

and

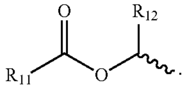

16. The method according to claim 11, wherein said compound is the compound of formula IIIb, the compound of formula IIIc, or the compound of formula IIId, and wherein $R_3$ is selected from H, -Me, -Et, —Pr, -iPr, -Bu, -tBu, -iBu, pentyl, isopentyl, and hexyl; -benzyl, polyethylenglycolyl,

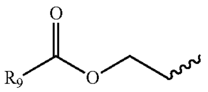

and

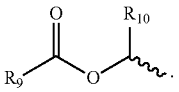

17. The method according to claim 11, wherein said compound is the compound of formula IIIb, the compound of formula IIIc, or the compound of formula IIId, and wherein $R_4$ is selected from H, —C(═O)-Me, —C(═O)-Et, —C(═O)—Pr, —C(═O)-iPr, —C(═O)—Bu, and —C(═O)-tBu; —C(═O)-benzyl, polyethylenglycolyl,

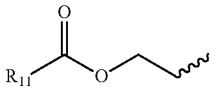

and

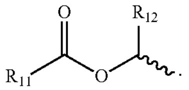

18. The method according to claim 11, wherein said compound is the compound of formula IIIb, the compound of formula IIIc, or the compound of formula IIId, and wherein one of $R_{13}$ and $R_{14}$ is H and the other is selected from H, F, Cl, Br, I, aryl, straight or branched $C_{1-8}$ alkyl, $—CH_2(CH_2)_p$-aryl, and —CH═CH-aryl.

19. The method according to claim 11, wherein the compound is selected from

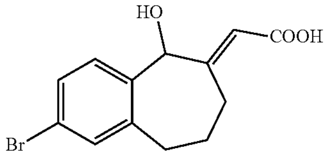

-continued

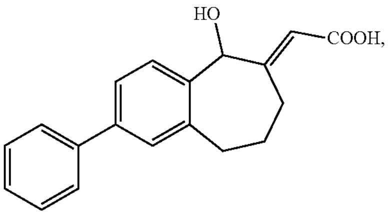

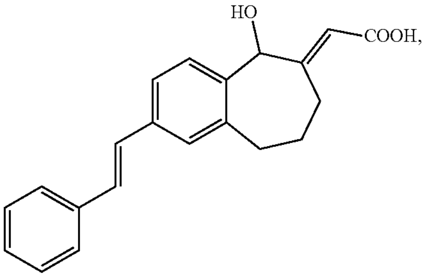

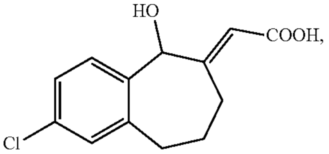

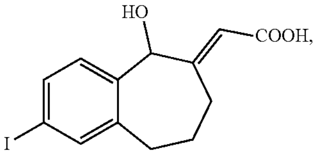

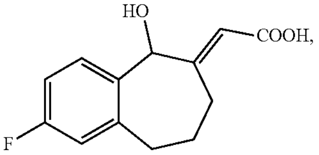

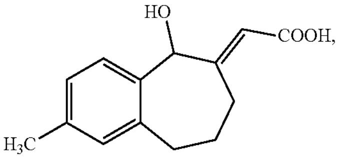

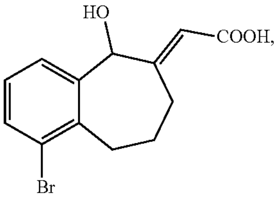

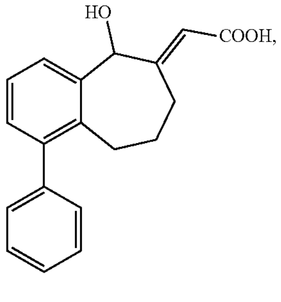

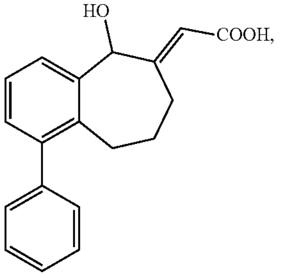

-continued
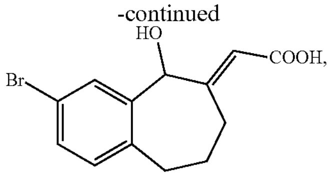
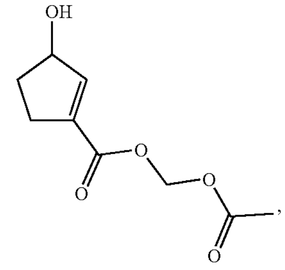
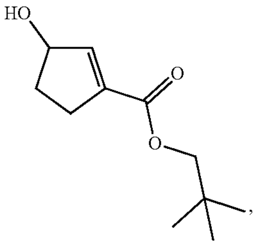
* * * * *

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: CD14 (F)

<400> SEQUENCE: 1
aatctaccga ccatggagc 19

<210> SEQ ID NO 2
<211> LENGTH: 19
<212> TYPE: DNA
<213> ORGANISM: Artificial Sequence
<220> FEATURE:
<223> OTHER INFORMATION: CD14 (R)

<400> SEQUENCE: 2

-continued

```
actttcctcg tctagctcg                                                    19


<210> SEQ ID NO 3
<211> LENGTH: 20
<212> TYPE: DNA
<213> ORGANISM: Artificial Sequence
<220> FEATURE:
<223> OTHER INFORMATION: IL-6 (F)

<400> SEQUENCE: 3

ctctgggaaa tcgtggaaat                                                   20


<210> SEQ ID NO 4
<211> LENGTH: 20
<212> TYPE: DNA
<213> ORGANISM: Artificial Sequence
<220> FEATURE:
<223> OTHER INFORMATION: IL-6 (R)

<400> SEQUENCE: 4

ccagtttggt agcatccatc                                                   20


<210> SEQ ID NO 5
<211> LENGTH: 21
<212> TYPE: DNA
<213> ORGANISM: Artificial Sequence
<220> FEATURE:
<223> OTHER INFORMATION: MMP9 (F)

<400> SEQUENCE: 5

cagccgactt ttgtggtctt c                                                 21


<210> SEQ ID NO 6
<211> LENGTH: 20
<212> TYPE: DNA
<213> ORGANISM: Artificial Sequence
<220> FEATURE:
<223> OTHER INFORMATION: MMP9 (R)

<400> SEQUENCE: 6

cggccgtaga gactgcttct                                                   20


<210> SEQ ID NO 7
<211> LENGTH: 19
<212> TYPE: DNA
<213> ORGANISM: Artificial Sequence
<220> FEATURE:
<223> OTHER INFORMATION: GFAP (F)

<400> SEQUENCE: 7

ggagatgcgg gatggtgag                                                    19


<210> SEQ ID NO 8
<211> LENGTH: 20
<212> TYPE: DNA
<213> ORGANISM: Artificial Sequence
<220> FEATURE:
<223> OTHER INFORMATION: GFAP (R)

<400> SEQUENCE: 8

accacgtcct tgtgctcctg                                                   20


<210> SEQ ID NO 9
<211> LENGTH: 20
<212> TYPE: DNA
```

-continued

```
<213> ORGANISM: Artificial Sequence
<220> FEATURE:
<223> OTHER INFORMATION: Rpl13a (F)

<400> SEQUENCE: 9

ggaggggcag gttctggtat                                              20


<210> SEQ ID NO 10
<211> LENGTH: 20
<212> TYPE: DNA
<213> ORGANISM: Artificial Sequence
<220> FEATURE:
<223> OTHER INFORMATION: Rpl13a (R)

<400> SEQUENCE: 10

tgttgatgcc ttcacagcgt                                              20


<210> SEQ ID NO 11
<211> LENGTH: 20
<212> TYPE: DNA
<213> ORGANISM: Artificial Sequence
<220> FEATURE:
<223> OTHER INFORMATION: SDHA (F)

<400> SEQUENCE: 11

gcccatgcca gggaagatta                                              20


<210> SEQ ID NO 12
<211> LENGTH: 20
<212> TYPE: DNA
<213> ORGANISM: Artificial Sequence
<220> FEATURE:
<223> OTHER INFORMATION: SDHA (R)

<400> SEQUENCE: 12

tgttccccaa acggcttctt                                              20
```